US007452665B2

(12) United States Patent
Barnes

(10) Patent No.: US 7,452,665 B2
(45) Date of Patent: Nov. 18, 2008

(54) DNA POLYMERASES WITH ENHANCED LENGTH OF PRIMER EXTENSION

(75) Inventor: Wayne M. Barnes, Unversity City, MO (US)

(73) Assignee: Takara Bio Inc. (JP)

( * ) Notice: Subject to any disclaimer, the term of this patent is extended or adjusted under 35 U.S.C. 154(b) by 756 days.

(21) Appl. No.: 09/981,002

(22) Filed: Oct. 17, 2001

(65) Prior Publication Data

US 2003/0049634 A1 Mar. 13, 2003

Related U.S. Application Data

(63) Continuation of application No. 08/931,818, filed on Sep. 16, 1997, now Pat. No. 6,410,277, and a continuation-in-part of application No. 08/486,535, filed on Jun. 7, 1995, which is a continuation-in-part of application No. 08/021,623, filed on Feb. 19, 1993, now Pat. No. 5,436,149.

(51) Int. Cl.
C12Q 1/68 (2006.01)
C12P 19/34 (2006.01)

(52) U.S. Cl. .................. 435/6; 435/91.1; 435/91.2; 435/975

(58) Field of Classification Search ............ 435/6, 435/91.2; 536/22.1, 23.1
See application file for complete search history.

(56) References Cited

U.S. PATENT DOCUMENTS

| | | | |
|---|---|---|---|
| 4,683,202 A | 7/1987 | Mullis | |
| 4,795,699 A | 1/1989 | Tabor et al. | |
| 4,921,794 A | 5/1990 | Tabor et al. | |
| 4,946,786 A | 8/1990 | Tabor et al. | |
| 5,001,050 A | 3/1991 | Blanco et al. | |
| 5,075,216 A | 12/1991 | Innis et al. | |
| 5,079,352 A | 1/1992 | Gelfand et al. | |
| 5,210,036 A | 5/1993 | Comb et al. | |
| 5,322,785 A | 6/1994 | Comb et al. | |
| 5,352,778 A | 10/1994 | Comb et al. | |
| 5,374,553 A | 12/1994 | Gelfand et al. | |
| 5,413,924 A * | 5/1995 | Kosak et al. ............... | 435/177 |
| 5,436,149 A | 7/1995 | Barnes | |
| 5,456,149 A | 10/1995 | Elsenheimer et al. | |
| 5,466,591 A | 11/1995 | Abramson et al. | |
| 5,489,523 A | 2/1996 | Mathur | |
| 5,500,363 A | 3/1996 | Comb et al. | |
| 5,512,462 A | 4/1996 | Cheng | |
| 5,545,552 A | 8/1996 | Mathur | |
| 5,556,772 A | 9/1996 | Sorge et al. | |
| 5,618,702 A * | 4/1997 | Scanlon ..................... | 435/91.2 |
| 6,410,277 B1 * | 6/2002 | Barnes ..................... | 435/91.2 |

FOREIGN PATENT DOCUMENTS

| | | |
|---|---|---|
| EP | 0265293 | 4/1988 |
| EP | 0386857 | 9/1990 |
| EP | 416755 | 3/1991 |
| WO | WO 89/06691 | 7/1989 |
| WO | WO 91/02090 | 2/1991 |
| WO | WO 92/06188 | 4/1992 |
| WO | WO 92/06200 | 4/1992 |
| WO | WO 92/09689 | 6/1992 |
| WO | WO 94/26766 | * 11/1994 |

OTHER PUBLICATIONS

Livingston, David. M. et al. "Affinity Chromatography of Avian Type C Viral Reverse Transcriptase: Studies with Rous Sarcoma Virus Transformed Rate Cells" Virology 50, 388-395 (1972).

Mattila, P. et al., "Fidelity of DNA synthesis by the *Thermococcus litoralis* DNA polymerase-an extremely heat stable enzyme with proofreading activity", Nucl. Acids Res. 19(18): 4967-4973 (1991).

Lundberg, K.S., "High-fidelity Amplification using a Thermo-stable DNA Polymerase Isolated from *Pyrococcus fusiosus*", Gene 108:1-6 (1991).

Ohler, L.D. et al., "Optimization of Long-distance PCR Using Transposon-based Model System", PCR Methods and Applications, pp. 51-59, (1992).

Barnes, W., "The fidelity of Taq Polymerase Catalyzing PCR is Improved by and N-terminal Deletion", Gene, 112: 29-35 (1992).

Uemori, Takashi et al. "Organization and Nucleotide Sequence of the DNA Polymerase Gene from the Archaeon *Pyroccoccus furiosus*", Nucliec Acids Research, 21:259-265 (1993).

Barnes, W., "PCR Amplification of up to 35-kb DNA with high Fidelity and High Yield from λ Bacteriophage Templates", PNAS 91: 2216-2220 (1994).

Cheng, S. et al., "Effective Amplification of Long Targets from Cloned Inserts and Human Genomic DNA", PNAS 91:5695-5699 (1994).

Anonymous, "Recombinant VentR™ DNA Polymerase", The NEB Transcript 3:4 (1991).

Lawyer, F.C., et al., "High-level Expression, Purification, and Enzymatic Characterization of Full-Length Thermus *Aquaticus* DNA Polymerase and a Truncated form Deficient in 5' to 3' Exonuclease Activity", PCR Meth. and Appl. 2:275-287 (1993).

(Continued)

*Primary Examiner*—Gary Benzion
*Assistant Examiner*—Christopher M. Babic
(74) *Attorney, Agent, or Firm*—Sonnenschein Nath & Rosenthal LLP

(57) ABSTRACT

A formulation and kit of thermostable or other DNA polymerases comprising at least one thermostable or other DNA polymerase which lacks 3'-exonuclease activity, and at least one thermostable DNA polymerase exhibiting 3'-exonuclease activity. Also provided is an improved method for enzymatic extension of DNA strands, especially while, but not limited to, amplifying nucleic acid sequences by polymerase chain reaction wherein the above formulation is made and used to catalyze primer extension.

5 Claims, 9 Drawing Sheets

OTHER PUBLICATIONS

Perrino, F.W., et al., "Proofreading by the ε Subunit of *Escherichia coli* DNA Polymerase III Increases the Fidelity of Calf Thymus DNA Polymerase α", Proc. Natl. Acad. Sci. 86: 3085-88.

Yu Sheng Zhu, et al., "The Use of Exonuclease III for Polymerase Chain Reaction Sterilization", Nucleic Acids Res. 19:2511 (1991).

Carballeria et al., "Purification of a Thermostable DNA Polymerase from *Thermus thermophilus* HB8, Useful in the Polymerase Chain Reaction," Biotechniques, 1990, pp. 276-281, vol. 9.

* cited by examiner

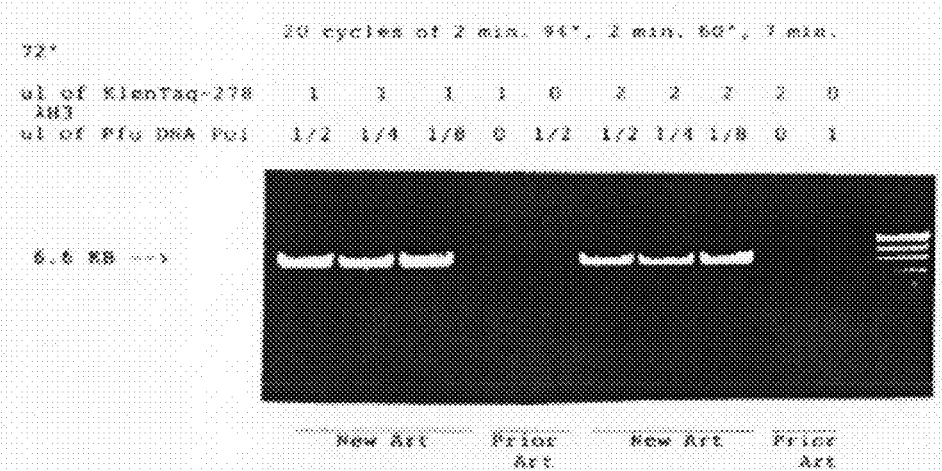

2 min. at indicated 99°, 98° or 97°, 10 min. 65° per cycle, 20 cycles.

99°    AmpliTaq .8 .4 .2    KlenTaq1 1/4 1/8 1/16    <-- ul per 100 ul reaction.

<-- 2 KB product size

98°    AmpliTaq .8 .4 .2    KlenTaq1 1/4 1/8 1/16    <-- ul per 100 ul reaction.

<-- 2 KB product size

97°    AmpliTaq .8 .4 .2    KlenTaq1 1/4 1/8 1/16    <-- ul per 100 ul reaction.

<-- 2 KB product size 20 cycles of 2 min. 94°, 2 min. 60°, 10 min. 72°

| ul of KlenTaq-278 | 1 | 1 | 1 | 1 | 1 | 1 | 0 |
| ul of Pfu DNA Pol | 1/2 | 1/4 | 1/8 | 1/16 | 1/32 | 0 | 1/2 |

<--6.6KB 20 cycles of 2 min. 95°, 1 min. 60°, 30 min. 72°

| ul of KlenTaq-278 | 1 | 1 | 1 | 1 | 1 |
| ul of Pfu DNA Pol | 1 | 1/4 | 1/16 | 1/64 | 0 |

λH3

<--6.6KB

| Channel: | 1 | 2 | 3 | 4 | 5 | 6 | 7 | 8 |
|---|---|---|---|---|---|---|---|---|
| Template DNA: | λplac5 | λpcytI | λpcytI | λplac5 | λplac5 | λK138 | λK138 | λK138 |
| ng of template: | 1 | 1 | 10 | 1 | 10 | 1 | 10 | 10 |
| primer 1 SEQ ID NO: | 9 | 7 | 7 | 10 | 10 | 7 | 7 | 9 |
| primer 2 SEQ ID NO: | 8 | 8 | 8 | 8 | 8 | 8 | 8 | 8 |
| Size of PCR product Expected, in kb: | 8.4 | 12.5 | 12.5 | 15 | 15 | 18 | 18 | 19.7 |

SEQUENCE LISTING

<160> NUMBER OF SEQ ID NOS: 29

<210> SEQ ID NO 1
<211> LENGTH: 36
<212> TYPE: DNA
<213> ORGANISM: Thermus aquaticus
<220> FEATURE:
<221> NAME/KEY: CDS
<222> LOCATION: (6)..(35)

<400> SEQUENCE: 1

```
gagcc atg ggc ctc ctc cac gag ttc ggc ctt ctg g                    36
      Met Gly Leu Leu His Glu Phe Gly Leu Leu
```

-continued

```
                1               5                      10

<210> SEQ ID NO 2
<211> LENGTH: 10
<212> TYPE: PRT
<213> ORGANISM: Thermus aquaticus

<400> SEQUENCE: 2

Met Gly Leu Leu His Glu Phe Gly Leu Leu
1               5                   10

<210> SEQ ID NO 3
<211> LENGTH: 35
<212> TYPE: DNA
<213> ORGANISM: Thermus aquaticus
<220> FEATURE:
<221> NAME/KEY: CDS
<222> LOCATION: (2)..(34)

<400> SEQUENCE: 3 g gac tgg ctc tcc gcc aag gag tag taa gct tcg c            35
  Asp Trp Leu Ser Ala Lys Glu         Ala Ser
  1               5

<210> SEQ ID NO 4
<211> LENGTH: 7
<212> TYPE: PRT
<213> ORGANISM: Thermus aquaticus

<400> SEQUENCE: 4

Asp Trp Leu Ser Ala Lys Glu
1               5

<210> SEQ ID NO 5
<211> LENGTH: 6714
<212> TYPE: DNA
<213> ORGANISM: Expression vector
<220> FEATURE:
<221> NAME/KEY: CDS
<222> LOCATION: (1)..(1665)

<400> SEQUENCE: 5 atg ggc ctc ctc cac gag ttc ggc ctt ctg gaa agc ccc aag gcc ctg      48
Met Gly Leu Leu His Glu Phe Gly Leu Leu Glu Ser Pro Lys Ala Leu
1               5                   10                  15 gag gag gcc ccc tgg ccc ccg ccg gaa ggg gcc ttc gtg ggc ttt gtg      96
Glu Glu Ala Pro Trp Pro Pro Pro Glu Gly Ala Phe Val Gly Phe Val
                20                  25                  30 ctt tcc cgc aag gag ccc atg tgg gcc gat ctt ctg gcc ctg gcc gcc     144
Leu Ser Arg Lys Glu Pro Met Trp Ala Asp Leu Leu Ala Leu Ala Ala
            35                  40                  45 gcc agg ggg ggc cgg gtc cac cgg gcc ccc gag cct tat aaa gcc ctc     192
Ala Arg Gly Gly Arg Val His Arg Ala Pro Glu Pro Tyr Lys Ala Leu
        50                  55                  60 agg gac ctg aag gag gcg cgg ggg ctt ctc gcc aaa gac ctg agc gtt     240
Arg Asp Leu Lys Glu Ala Arg Gly Leu Leu Ala Lys Asp Leu Ser Val
65                  70                  75                  80 ctg gcc ctg agg gaa ggc ctt ggc ctc ccg ccc ggc gac gac ccc atg     288
Leu Ala Leu Arg Glu Gly Leu Gly Leu Pro Pro Gly Asp Asp Pro Met
                85                  90                  95 ctc ctc gcc tac ctc ctg gac cct tcc aac acc acc ccc gag ggg gtg     336
Leu Leu Ala Tyr Leu Leu Asp Pro Ser Asn Thr Thr Pro Glu Gly Val
                100                 105                 110 gcc cgg cgc tac ggc ggg gag tgg acg gag gag gcg ggg gag cgg gcc     384
```

```
Ala Arg Arg Tyr Gly Gly Glu Trp Thr Glu Glu Ala Gly Glu Arg Ala
            115                 120                 125 gcc ctt tcc gag agg ctc ttc gcc aac ctg tgg ggg agg ctt gag ggg      432
Ala Leu Ser Glu Arg Leu Phe Ala Asn Leu Trp Gly Arg Leu Glu Gly
130                 135                 140 gag gag agg ctc ctt tgg ctt tac cgg gag gtg gag agg ccc ctt tcc      480
Glu Glu Arg Leu Leu Trp Leu Tyr Arg Glu Val Glu Arg Pro Leu Ser
145                 150                 155                 160 gct gtc ctg gcc cac atg gag gcc acg ggg gtg cgc ctg gac gtg gcc      528
Ala Val Leu Ala His Met Glu Ala Thr Gly Val Arg Leu Asp Val Ala
                165                 170                 175 tat ctc agg gcc ttg tcc ctg gag gtg gcc gag gag atc gcc cgc ctc      576
Tyr Leu Arg Ala Leu Ser Leu Glu Val Ala Glu Glu Ile Ala Arg Leu
                180                 185                 190 gag gcc gag gtc ttc cgc ctg gcc ggc cac ccc ttc aac ctc aac tcc      624
Glu Ala Glu Val Phe Arg Leu Ala Gly His Pro Phe Asn Leu Asn Ser
            195                 200                 205 cgg gac cag ctg gaa agg gtc ctc ttt gac gag cta ggg ctt ccc gcc      672
Arg Asp Gln Leu Glu Arg Val Leu Phe Asp Glu Leu Gly Leu Pro Ala
210                 215                 220 atc ggc aag acg gag aag acc ggc aag cgc tcc acc agc gcc gcc gtc      720
Ile Gly Lys Thr Glu Lys Thr Gly Lys Arg Ser Thr Ser Ala Ala Val
225                 230                 235                 240 ctg gag gcc ctc cgc gag gcc cac ccc atc gtg gag aag atc ctg cag      768
Leu Glu Ala Leu Arg Glu Ala His Pro Ile Val Glu Lys Ile Leu Gln
                245                 250                 255 tac cgg gag ctc acc aag ctg aag agc acc tac att gac ccc ttg ccg      816
Tyr Arg Glu Leu Thr Lys Leu Lys Ser Thr Tyr Ile Asp Pro Leu Pro
                260                 265                 270 gac ctc atc cac ccc agg acg ggc cgc ctc cac acc cgc ttc aac cag      864
Asp Leu Ile His Pro Arg Thr Gly Arg Leu His Thr Arg Phe Asn Gln
                275                 280                 285 acg gcc acg gcc acg ggc agg cta agt agc tcc gat ccc aac ctc cag      912
Thr Ala Thr Ala Thr Gly Arg Leu Ser Ser Ser Asp Pro Asn Leu Gln
            290                 295                 300 aac atc ccc gtc cgc acc ccg ctt ggg cag agg atc cgc cgg gcc ttc      960
Asn Ile Pro Val Arg Thr Pro Leu Gly Gln Arg Ile Arg Arg Ala Phe
305                 310                 315                 320 atc gcc gag gag ggg tgg cta ttg gtg gcc ctg gac tat agc cag ata     1008
Ile Ala Glu Glu Gly Trp Leu Leu Val Ala Leu Asp Tyr Ser Gln Ile
                325                 330                 335 gag ctc agg gtg ctg gcc cac ctc tcc ggc gac gag aac ctg atc cgg     1056
Glu Leu Arg Val Leu Ala His Leu Ser Gly Asp Glu Asn Leu Ile Arg
            340                 345                 350 gtc ttc cag gag ggg cgg gac atc cac acg gag acc gcc agc tgg atg     1104
Val Phe Gln Glu Gly Arg Asp Ile His Thr Glu Thr Ala Ser Trp Met
            355                 360                 365 ttc ggc gtc ccc cgg gag gcc gtg gac ccc ctg atg cgc cgg gcg gcc     1152
Phe Gly Val Pro Arg Glu Ala Val Asp Pro Leu Met Arg Arg Ala Ala
370                 375                 380 aag acc atc aac ttc ggg gtc ctc tac ggc atg tcg gcc cac cgc ctc     1200
Lys Thr Ile Asn Phe Gly Val Leu Tyr Gly Met Ser Ala His Arg Leu
385                 390                 395                 400 tcc cag gag cta gcc atc cct tac gag gag gcc cag gcc ttc att gag     1248
Ser Gln Glu Leu Ala Ile Pro Tyr Glu Glu Ala Gln Ala Phe Ile Glu
                405                 410                 415 cgc tac ttt cag agc ttc ccc aag gtg cgg gcc tgg att gag aag acc     1296
Arg Tyr Phe Gln Ser Phe Pro Lys Val Arg Ala Trp Ile Glu Lys Thr
            420                 425                 430
```

```
ctg gag gag ggc agg agg cgg ggg tac gtg gag acc ctc ttc ggc cgc      1344
Leu Glu Glu Gly Arg Arg Arg Gly Tyr Val Glu Thr Leu Phe Gly Arg
        435                 440                 445 cgc cgc tac gtg cca gac cta gag gcc cgg gtg aag agc gtg cgg gag      1392
Arg Arg Tyr Val Pro Asp Leu Glu Ala Arg Val Lys Ser Val Arg Glu
    450                 455                 460 gcg gcc gag cgc atg gcc ttc aac atg ccc gtc cag ggc acc gcc gcc      1440
Ala Ala Glu Arg Met Ala Phe Asn Met Pro Val Gln Gly Thr Ala Ala
465                 470                 475                 480 gac ctc atg aag ctg gct atg gtg aag ctc ttc ccc agg ctg gag gaa      1488
Asp Leu Met Lys Leu Ala Met Val Lys Leu Phe Pro Arg Leu Glu Glu
                485                 490                 495 atg ggg gcc agg atg ctc ctt cag gtc cac gac gag ctg gtc ctc gag      1536
Met Gly Ala Arg Met Leu Leu Gln Val His Asp Glu Leu Val Leu Glu
            500                 505                 510 gcc cca aaa gag agg gcg gag gcc gtg gcc cgg ctg gcc aag gag gtc      1584
Ala Pro Lys Glu Arg Ala Glu Ala Val Ala Arg Leu Ala Lys Glu Val
        515                 520                 525 atg gag ggg gtg tat ccc ctg gcc gtg ccc ctg gag gtg gag gtg ggg      1632
Met Glu Gly Val Tyr Pro Leu Ala Val Pro Leu Glu Val Glu Val Gly
    530                 535                 540 ata ggg gag gac tgg ctc tcc gcc aag gag tag taagcttatc gatgataagc    1685
Ile Gly Glu Asp Trp Leu Ser Ala Lys Glu
545                 550 tgtcaaacat gagaattagc ccgcctaatg agcgggcttt ttttttaattc ttgaagacga   1745
aagggcctcg tgatacgcct attttttatag gttaatgtca tgataataat ggtttcttag  1805
cgtcaaagca accatagtac gcgccctgta gcggcgcatt aagcgcgccg ggtgtggtgg   1865
ttacgcgcag cgtgaccgct acacttgcca gcgccctagc gcccgctcct ttcgctttct   1925
tcccttcctt tctcgccacg ttcgccggct ttccccgtca agctctaaat cggggggctcc  1985
ctttagggtt ccgatttagt gctttacggc acctcgaccc caaaaaactt gatttgggtg   2045
atggttcacg tagtgggcca tcgccctgat agacggtttt tcgccctttg acgttggagt   2105
ccacgttctt taatagtgga ctcttgttcc aaacttgaac aacactcaac cctatctcgg   2165
gctattcttt tgatttataa gggattttgc cgatttcggc ctattggtta aaaaatgagc   2225
tgatttaaca aaaatttaac gcgaatttta acaaaatatt aacgtttaca atttcaggtg   2285
gcacttttcg gggaaatgtg cgcggaaccc ctatttgttt attttcctaa atacattcaa   2345
atatgtatcc gctcatgaga caataaccct gataaatgct tcaataatat tgaaaaagga   2405
agagtatgag tattcaacat ttccgtgtcg cccttattcc cttttttgcg gcattttgcc   2465
ttcctgtttt tgctcaccca gaaacgctgg tgaaagtaaa agatgctgaa gatcagttgg   2525
gtgcacgagt gggttacatc gaactggatc tcaacagcgg taagatcctt gagagttttc   2585
gccccgaaga acgttttcca atgatgagca cttttaaagt tctgctatgt ggcgcggtat   2645
tatcccgtgt tgacgccggg caagagcaac tcggtcgccg catacactat tctcagaatg   2705
acttggttga gtactcacca gtcacagaaa agcatcttac ggatggcatg acagtaagag   2765
aattatgcag tgctgccata accatgagtg ataacactgc ggccaactta cttctgacaa   2825
cgatcggagg accgaaggag ctaaccgctt ttttgcacaa catgggggat catgtaactc   2885
gccttgatcg ttgggaaccg gagctgaatg aagccatacc aaacgacgag cgtgacacca   2945
cgatgcctgc agcaatggca acaacgttgc gcaaactatt aactggcgaa ctacttactc   3005
tagcttcccg gcaacaatta atagactgga tggaggcgga taaagttgca ggaccacttc   3065
tgcgctcggc ccttccggct ggctggttta ttgctgataa atctggagcc ggtgagcgtg   3125
```

```
ggtctcgcgg tatcattgca gcactggggc cagatggtaa gccctcccgt atcgtagtta   3185
tctacacgac ggggagtcag gcaactatgg atgaacgaaa tagacagatc gctgagatag   3245
gtgcctcact gattaagcat tggtaactgt cagaccaagt ttactcatat atactttaga   3305
ttgatttaaa acttcatttt taatttaaaa ggatctaggt gaagatcctt tttgataatc   3365
tcatgaccaa aatcccttaa cgtgagtttt cgttccactg agcgtcagac cccgtagaaa   3425
agatcaaagg atcttcttga tccttttttt tctgcgcgt aatctgctgc ttgcaaacaa   3485
aaaaaccacc gctaccagcg gtggtttgtt tgccggatca agagctacca actcttttc   3545 cgaaggtaac tggcttcagc agagcgcaga taccaaatac tgtccttcta gtgtagccgt   3605
agttaggcca ccacttcaag aactctgtag caccgcctac atacctcgct ctgctaatcc   3665
tgttaccagt ggctgctgcc agtggcgata agtcgtgtct taccgggttg gactcaagac   3725
gatagttacc ggataaggcg cagcggtcgg gctgaacggg gggttcgtgc acacagccca   3785
gcttggagcg aacgacctac accgaactga gatacctaca gcgtgagcta tgagaaagcg   3845
ccacgcttcc cgaagggaga aaggcggaca ggtatccggt aagcggcagg gtcggaacag   3905
gagagcgcac gagggagctt ccaggggaa acgcctggta tctttatagt cctgtcgggt   3965
ttcgccacct ctgacttgag cgtcgatttt tgtgatgctc gtcaggggg cggagcctat   4025 ggaaaaacgc cagcaacgcg ccttttttac ggttcctggc cttttgctgg ccttttgctc   4085
acatgttctt tcctgcgtta tcccctgatt ctgtggataa ccgtattacc gcctttgagt   4145
gagctgatac cgctcgccgc agccgaacga ccgagcgcag cgagtcagtg agcgaggaag   4205
cggaagagcg cctgatgcgg tattttctcc ttacgcatct gtgcggtatt tcacaccgca   4265
tatggtgcac tctcagtaca atctgctctg atgccgcata gttaagccag tatacactcc   4325
gctatcgcta cgtgactggg tcatggctgc gccccgacac ccgccaacac ccgctgacgc   4385
gccctgacgg gcttgtctgc tcccggcatc cgcttacaga caagctgtga ccgtctccgg   4445
gagctgcatg tgtcagaggt tttcaccgtc atcaccgaaa cgcgcgaggc agaacgccat   4505
caaaaataat tcgcgtctgg ccttcctgta gccagctttc atcaacatta atgtgagcg   4565 agtaacaacc cgtcggattc tccgtgggaa caaacggcgg attgaccgta atgggatagg   4625
ttacgttggt gtagatgggc gcatcgtaac cgtgcatctg ccagtttgag gggacgacga   4685
cagtatcggc ctcaggaaga tcgcactcca gccagctttc cggcaccgct tctggtgccg   4745
gaaaccaggc aaagcgccat tcgccattca ggctgcgcaa ctgttgggaa gggcgatcgg   4805
tgcgggcctc ttcgctatta cgccagctgg cgaaaggggg atgtgctgca aggcgattaa   4865
gttgggtaac gccagggttt tcccagtcac gacgttgtaa aacgacggcc agtgaatccg   4925
taatcatggt catagctgtt tcctgtgtga aattgttatc cgctcacaat tccacacaac   4985
atacgagccg gaagcataaa gtgtaaagcc tggggtgcct aatgagtgag ctaactcaca   5045
ttaattgcgt tgcgctcact gcccgctttc cagtcgggaa acctgtcgtg ccagctgcat   5105
taatgaatcg gccaacgcgc ggggagaggc ggtttgcgta ttgggcgcca gggtggtttt   5165
tcttttcacc agtgagacgg gcaacagctg attgcccttc accgcctggc cctgagagag   5225
ttgcagcaag cggtccacgc tggtttgccc cagcaggcga aaatcctgtt tgatggtggt   5285
tgacggcggg atataacatg agctgtcttc ggtatcgtcg tatcccacta ccgagatatc   5345
cgcaccaacg cgcagcccgg actcggtaat ggcgcgcatt gcgcccagcg ccatctgatc   5405
gttggcaacc agcatcgcag tgggaacgat gccctcattc agcatttgca tggtttgttg   5465
```

-continued

```
aaaaccggac atggcactcc agtcgccttc ccgttccgct atcggctgaa tttgattgcg    5525
agtgagatat ttatgccagc cagccagacg cagacgcgcc gagacagaac ttaatgggcc    5585
cgctaacagc gcgatttgct ggtgacccaa tgcgaccaga tgctccacgc ccagtcgcgt    5645
accgtcttca tgggagaaaa taatactgtt gatgggtgtc tggtcagaga catcaagaaa    5705
taacgccgga acattagtgc aggcagcttc cacagcaatg gcatcctggt catccagcgg    5765
atagttaatg atcagcccac tgacgcgttg cgcgagaaga ttgtgcaccg ccgctttaca    5825
ggcttcgacg ccgcttcgtt ctaccatcga caccaccacg ctggcaccca gttgatcggc    5885
gcgagattta atcgccgcga caatttgcga cggcgcgtgc agggccagac tggaggtggc    5945
aacgccaatc agcaacgact gtttgcccgc cagttgttgt gccacgcggt tgggaatgta    6005
attcagctcc gccatcgccg cttccacttt ttcccgcgtt ttcgcagaaa cgtggctggc    6065
ctggttcacc acgcgggaaa cggtctgata agagacaccg gcatactctg cgacatcgta    6125
taacgttact ggtttcacat tcaccaccct gaattgactc tcttccgggc gctatcatgc    6185
cataccgcga aggttttgc gccattcgat ggtgtcccag tgaatccgta atcatggtca    6245
tagctgtttc ctgtgtgaaa ttgttatccg ctcacaattc cacacattat acgagccgga    6305
agcataaagt gtaaagcctg gggtgcctaa tgagtgagct aactcacatt aattgcgttg    6365
cgctcactgc ccgctttcca gtcgggaaac ctgtcgtgcc agctgcatta atgaatcgga    6425
gcttactccc catcccctg ttgacaatta atcatcggct cgtataatgt gtggaattgt    6485
gagcggataa caatttcaca caggaaacag gatcgatcca gcttactccc catcccctg    6545 ttgacaatta atcatcggct cgtataatgt gtggaattgt gagcggataa caatttcaca    6605
caggaaacag gatctgggcc cttcgaaatt aatacgactc actataggga gaccacaacg    6665
gtttccctct agaaataatt tgtttaact ttaagaagga gatatatcc                 6714
```

<210> SEQ ID NO 6
<211> LENGTH: 554
<212> TYPE: PRT
<213> ORGANISM: Expression vector

<400> SEQUENCE: 6

```
Met Gly Leu Leu His Glu Phe Gly Leu Leu Glu Ser Pro Lys Ala Leu
1               5                   10                  15

Glu Glu Ala Pro Trp Pro Pro Pro Glu Gly Ala Phe Val Gly Phe Val
            20                  25                  30

Leu Ser Arg Lys Glu Pro Met Trp Ala Asp Leu Ala Leu Ala Ala
        35                  40                  45

Ala Arg Gly Gly Arg Val His Arg Ala Pro Glu Pro Tyr Lys Ala Leu
    50                  55                  60

Arg Asp Leu Lys Glu Ala Arg Gly Leu Leu Ala Lys Asp Leu Ser Val
65                  70                  75                  80

Leu Ala Leu Arg Glu Gly Leu Gly Leu Pro Gly Asp Asp Pro Met
                85                  90                  95

Leu Leu Ala Tyr Leu Leu Asp Pro Ser Asn Thr Thr Pro Glu Gly Val
            100                 105                 110

Ala Arg Arg Tyr Gly Gly Glu Trp Thr Glu Glu Ala Gly Glu Arg Ala
        115                 120                 125

Ala Leu Ser Glu Arg Leu Phe Ala Asn Leu Trp Gly Arg Leu Glu Gly
    130                 135                 140

Glu Glu Arg Leu Leu Trp Leu Tyr Arg Glu Val Glu Arg Pro Leu Ser
145                 150                 155                 160
```

```
Ala Val Leu Ala His Met Glu Ala Thr Gly Val Arg Leu Asp Val Ala
                165                 170                 175

Tyr Leu Arg Ala Leu Ser Leu Glu Val Ala Glu Ile Ala Arg Leu
            180                 185                 190

Glu Ala Glu Val Phe Arg Leu Ala Gly His Pro Phe Asn Leu Asn Ser
        195                 200                 205

Arg Asp Gln Leu Glu Arg Val Leu Phe Asp Leu Gly Leu Pro Ala
    210                 215                 220

Ile Gly Lys Thr Glu Lys Thr Gly Lys Arg Ser Thr Ser Ala Ala Val
225                 230                 235                 240

Leu Glu Ala Leu Arg Glu Ala His Pro Ile Val Glu Lys Ile Leu Gln
                245                 250                 255

Tyr Arg Glu Leu Thr Lys Leu Lys Ser Thr Tyr Ile Asp Pro Leu Pro
            260                 265                 270

Asp Leu Ile His Pro Arg Thr Gly Arg Leu His Thr Arg Phe Asn Gln
        275                 280                 285

Thr Ala Thr Ala Thr Gly Arg Leu Ser Ser Ser Asp Pro Asn Leu Gln
    290                 295                 300

Asn Ile Pro Val Arg Thr Pro Leu Gly Gln Arg Ile Arg Arg Ala Phe
305                 310                 315                 320

Ile Ala Glu Glu Gly Trp Leu Leu Val Ala Leu Asp Tyr Ser Gln Ile
                325                 330                 335

Glu Leu Arg Val Leu Ala His Leu Ser Gly Asp Glu Asn Leu Ile Arg
            340                 345                 350

Val Phe Gln Glu Gly Arg Asp Ile His Thr Glu Thr Ala Ser Trp Met
        355                 360                 365

Phe Gly Val Pro Arg Glu Ala Val Asp Pro Leu Met Arg Arg Ala Ala
    370                 375                 380

Lys Thr Ile Asn Phe Gly Val Leu Tyr Gly Met Ser Ala His Arg Leu
385                 390                 395                 400

Ser Gln Glu Leu Ala Ile Pro Tyr Glu Glu Ala Gln Ala Phe Ile Glu
                405                 410                 415

Arg Tyr Phe Gln Ser Phe Pro Lys Val Arg Ala Trp Ile Glu Lys Thr
            420                 425                 430

Leu Glu Glu Gly Arg Arg Arg Gly Tyr Val Glu Thr Leu Phe Gly Arg
        435                 440                 445

Arg Arg Tyr Val Pro Asp Leu Glu Ala Arg Val Lys Ser Val Arg Glu
    450                 455                 460

Ala Ala Glu Arg Met Ala Phe Asn Met Pro Val Gln Gly Thr Ala Ala
465                 470                 475                 480

Asp Leu Met Lys Leu Ala Met Val Lys Leu Phe Pro Arg Leu Glu Glu
                485                 490                 495

Met Gly Ala Arg Met Leu Leu Gln Val His Asp Glu Leu Val Leu Glu
            500                 505                 510

Ala Pro Lys Glu Arg Ala Glu Ala Val Ala Arg Leu Ala Lys Glu Val
        515                 520                 525

Met Glu Gly Val Tyr Pro Leu Ala Val Pro Leu Glu Val Glu Val Gly
    530                 535                 540

Ile Gly Glu Asp Trp Leu Ser Ala Lys Glu
545                 550

<210> SEQ ID NO 7
<211> LENGTH: 27
```

<212> TYPE: DNA
<213> ORGANISM: Bacteriophage lambda

<400> SEQUENCE: 7
gcttatctgc ttctcataga gtcttgc                                        27

<210> SEQ ID NO 8
<211> LENGTH: 27
<212> TYPE: DNA
<213> ORGANISM: Bacteriophage lambda

<400> SEQUENCE: 8
ataacgatca tatacatggt tctctcc                                        27

<210> SEQ ID NO 9
<211> LENGTH: 27
<212> TYPE: DNA
<213> ORGANISM: Bacteriophage lambda

<400> SEQUENCE: 9
ttttgctggg tcaggttgtt ctttagg                                        27

<210> SEQ ID NO 10
<211> LENGTH: 28
<212> TYPE: DNA
<213> ORGANISM: Escherichia coli

<400> SEQUENCE: 10
ggaagcttat ttttgacacc agaccaac                                       28

<210> SEQ ID NO 11
<211> LENGTH: 37
<212> TYPE: DNA
<213> ORGANISM: Zea mays

<400> SEQUENCE: 11
gtgatggatc cttcagcttc ccgagttcag caggcgg                             37

<210> SEQ ID NO 12
<211> LENGTH: 37
<212> TYPE: DNA
<213> ORGANISM: Zea mays

<400> SEQUENCE: 12
ggtctcgagc gaagcttccc tatagctttg cgaagag                             37

<210> SEQ ID NO 13
<211> LENGTH: 37
<212> TYPE: DNA
<213> ORGANISM: Thermus aquaticus

<400> SEQUENCE: 13
gagccatggc caacctgtgg gggaggcttg aggggga                             37

<210> SEQ ID NO 14
<211> LENGTH: 36
<212> TYPE: DNA
<213> ORGANISM: Thermus aquaticus

<400> SEQUENCE: 14
agtttggcag cctcctccac gagttcggcc ttctgg                              36

<210> SEQ ID NO 15

```
<211> LENGTH: 32
<212> TYPE: DNA
<213> ORGANISM: Thermus aquaticus

<400> SEQUENCE: 15
ggactggctc tccgccaagg agtgatacca cc                               32

<210> SEQ ID NO 16
<211> LENGTH: 36
<212> TYPE: DNA
<213> ORGANISM: Thermus flavis

<400> SEQUENCE: 16
agtttggaag cctcctccac gagttcggcc tcctgg                           36

<210> SEQ ID NO 17
<211> LENGTH: 35
<212> TYPE: DNA
<213> ORGANISM: Thermus flavis

<400> SEQUENCE: 17
ggactggctc tccgccaagg agtagggggg tcctg                            35

<210> SEQ ID NO 18
<211> LENGTH: 39
<212> TYPE: DNA
<213> ORGANISM: Bacillus thuringiensis

<400> SEQUENCE: 18
gcgaagcttc tcgagttacg ctcaatatgg agttgcttc                        39

<210> SEQ ID NO 19
<211> LENGTH: 43
<212> TYPE: DNA
<213> ORGANISM: Bacillus thuringiensis

<400> SEQUENCE: 19
ccgagatctc catggatcca agaatcaag ataagcatca aag                    43

<210> SEQ ID NO 20
<211> LENGTH: 36
<212> TYPE: DNA
<213> ORGANISM: Bacteriophage lambda

<400> SEQUENCE: 20
gggcggcgac ctcgcgggtt ttcgctattt atgaaa                           36

<210> SEQ ID NO 21
<211> LENGTH: 33
<212> TYPE: DNA
<213> ORGANISM: Escherichia coli

<400> SEQUENCE: 21
cgacggccag tgaatccgta atcatggtca tag                              33

<210> SEQ ID NO 22
<211> LENGTH: 33
<212> TYPE: DNA
<213> ORGANISM: Escherichia coli

<400> SEQUENCE: 22
accagccatc gccatctgct gcacgcggaa gaa                              33
```

```
<210> SEQ ID NO 23
<211> LENGTH: 36
<212> TYPE: DNA
<213> ORGANISM: Escherichia coli

<400> SEQUENCE: 23
ctatgaccat gattacggat tcactggccg tcgttt                                 36

<210> SEQ ID NO 24
<211> LENGTH: 33
<212> TYPE: DNA
<213> ORGANISM: Bacteriophage lambda

<400> SEQUENCE: 24
gcaagactct atgagaagca gataagcgat aag                                    33

<210> SEQ ID NO 25
<211> LENGTH: 33
<212> TYPE: DNA
<213> ORGANISM: Bacteriophage lambda

<400> SEQUENCE: 25
atcattattt gatttcaatt ttgtcccact ccc                                    33

<210> SEQ ID NO 26
<211> LENGTH: 33
<212> TYPE: DNA
<213> ORGANISM: Bacteriophage lambda

<400> SEQUENCE: 26
ggagagaacc atgtatatga tcgttatctg ggt                                    33

<210> SEQ ID NO 27
<211> LENGTH: 33
<212> TYPE: DNA
<213> ORGANISM: Bacteriophage lambda

<400> SEQUENCE: 27
gcgcacaaaa ccatagattg ctcttctgta agg                                    33

<210> SEQ ID NO 28
<211> LENGTH: 33
<212> TYPE: DNA
<213> ORGANISM: Escherichia coli

<400> SEQUENCE: 28
cccggttatt attattttg acaccagacc aac                                     33

<210> SEQ ID NO 29
<211> LENGTH: 36
<212> TYPE: DNA
<213> ORGANISM: Bacteriophage lambda

<400> SEQUENCE: 29
aggtcgccgc cccgtaacct gtcggatcac cggaaa                                 36
```

DNA POLYMERASES WITH ENHANCED LENGTH OF PRIMER EXTENSION

CROSS REFERENCE TO RELATED APPLICATION

This application is a continuation of U.S. patent application Ser. No. 08/931,818, filed Sep. 16, 1997 now issued as U.S. Pat. No. 6,410,277 B1, and is a continuation-in-part of co-pending U.S. patent application Ser. No. 08/483,535, filed Jun. 7, 1995, which is a continuation-in-part of U.S. patent application Ser. No. 08/021,623, filed Feb, 19, 1993 now issued as U.S. Pat. No. 5,436,149.

BACKGROUND OF THE INVENTION

The present invention is directed to DNA polymerases, and more particularly, to a novel formulation of DNA polymerases, which formulation of enzymes is capable of efficiently catalyzing the amplification by PCR (the polymerase chain reaction) of unusually long and faithful products.

DNA polymerase obtained from the hot springs bacterium *Thermus aquaticus* (Taq DNA polymerase) has been demonstrated to be quite useful in amplification of DNA, in DNA sequencing, and in related DNA primer extension techniques because it is thermostable. Thermostable is defined herein as having the ability to withstand temperatures up to 95° C. for many minutes without becoming irreversibly denatured, and the ability to polymerize DNA at high temperatures (60° to 75° C.). The DNA and amino acid sequences described by Lawyer et al., J. Biol. Chem. 264:6427 (1989), GenBank Accession No. J04639, define the gene encoding *Thermus aquaticus* DNA polymerase and the enzyme *Thermus aquaticus* DNA polymerase as those terms are used in this application. The highly similar DNA polymerase (Tfl DNA polymerase) expressed by the closely related bacterium *Thermus flavus* is defined by the DNA and amino acid sequences described by Akhmetzjanov, A. A., and Vakhitov, V. A. (1992) Nucleic Acids Research 20:5839, GenBank Accession No. X66105. These enzymes are representative of a family of DNA polymerases, also including *Thermus thermophilus* DNA polymerase, which are thermostable. These enzymes lack a 3'-exonuclease activity such as that which is effective for editing purposes in DNA polymerases such as *E. coli* DNA polymerase I, and phages T7, T3, and T4 DNA polymerases.

Gelfand et al., U.S. Pat. No. 4,889,818 describe a wild-type (abbreviation used here: WT), native *Thermus aquaticus* DNA polymerase. Gelfand et al., U.S. Pat. No. 5,079,352 describe a recombinant DNA sequence which encodes a mutein of *Thermus aquaticus* DNA polymerase from which the N-terminal 289 amino acids of *Thermus aquaticus* DNA polymerase have been deleted (claim 3 of '352, commercial name Stoffel Fragment, abbreviation used here: ST), and a recombinant DNA sequence which encodes a mutein of *Thermus aquaticus* DNA polymerase from which the N-terminal 3 amino acids of *Thermus aquaticus* DNA polymerase have been deleted (claim 4 of '352, trade name AmpliTaq, abbreviation used here: AT). Gelfand et al. report their muteins to be "fully active" in assays for DNA polymerase, but data as to their maximum thermostability is not presented.

Amplification of DNA spans by the polymerase chain reaction (PCR) has become an important and widespread tool of genetic analysis since the introduction of thermostable Taq DNA polymerase for its catalysis. However, one remaining limitation to prior art methods of PCR is the size of the product span that can be amplified. For full-length Taq DNA Polymerase and for N-terminally truncated variants such as Klentaq-278, Klentaq5 and Stoffel Fragment, PCR amplification apparently rapidly becomes inefficient or non-existent as the length of the target span exceeds 5-6 kb. This was shown even when 30 minutes was used during the extension step of each cycle.

Although there are several reports of inefficient but detectable amplification at 9-10 kb target length and one at 15 kb, most general applications are limited to 5 kb.

Kainze et al. (Analytical Biochem. 202:46-49 (1992)) report a PCR amplification of over 10 kb: a 10.9 kb and a 15.6 kb product, utilizing an enzyme of unpublished biological source (commercially available as "Hot Tub" DNA polymerase). Kainze et al. report achieving a barely visible band at 15.6 kb after 30 cycles, starting with 1 ng of λ DNA template per 100 ul of reaction volume. The efficiency of this amplification was shown to be relatively low, although a quantitative calculation of the efficiency was not presented. Attempts by Kainze et al. to make WT *Thermus aquaticus* DNA polymerase perform in the 10-15 kb size range were not successful, nor have successful results been reported by anyone else for any form of *Thermus aquaticus* DNA polymerase in this size range.

A DNA polymerase formulation capable of efficient amplification of DNA spans in excess of 6 kb would significantly expand the scope of applications of PCR. For instance, whole plasmids, and constructs the size of whole plasmids, could be prepared with this method, which would be especially valuable in cases in which a portion of the DNA in question is toxic or incompatible with plasmid replication when introduced into *E. coli*. If this thermostable DNA polymerase preparation simultaneously conferred increased fidelity to the PCR amplification, the resulting large products would be much more accurate, active and/or valuable in research and applications, especially in situations involving expression of the amplified sequence. If the thermostable DNA polymerase preparation allowed, in addition, more highly concentrated yields of pure product, this would enhance the method of PCR to the point where it could be used more effectively to replace plasmid replication as a means to produce desired DNA fragments in quantity.

SUMMARY OF THE INVENTION

Among the several objects of the invention, therefore, may be noted the provision of a formulation of DNA polymerases capable of efficiently catalyzing primer extension products of greater length than permitted by conventional formulations, including lengths up to at least 35 kilobases, that reduces the mutagenicity generated by the PCR process, particularly in comparison with prior art DNA polymerases and for any target lengths, that maximizes the yield of PCR target fragments and, concomitantly, enhances the intensity and sharpness of PCR product bands, without significant sacrifice in flexibility, specificity, and efficiency; and the provision of an improved process for amplification by PCR which can be utilized to reliably synthesize nucleic acid sequences of greater length and which can effectively utilize PCR products as primers.

Briefly, therefore, the present invention is directed to a novel formulation of thermostable DNA polymerases including at least one thermostable DNA polymerase lacking 3'-5' exonuclease activity and at least one thermostable DNA polymerase exhibiting 3'-5' exonuclease activity.

In another aspect, a kit for the synthesis of a polynucleotide is provided, comprising a first DNA polymerase which possesses 3'-5' exonuclease activity, and a second DNA polymerase which lacks 3'-5' exonuclease activity.

In another aspect, a kit for the synthesis of a polynucleotide is provided, comprising a first DNA polymerase which possesses 3'-5' exonuclease activity, and a second DNA polymerase which lacks 3'-5' exonuclease activity, wherein the first DNA polymerase is selected from the group consisting of *Pyrococcus furiosus* DNA polymerase, *Thermotoga maritima* DNA polymerase, *Thermococcus litoralis* DNA polymerase, and Pyrococus GB-D DNA polymerase, and the second DNA polymerase is selected from the group consisting of *Thermus aquaticus* DNA polymerase, (exo-) *Thermococcus literalis* DNA polymerase, (exo-) *Pyrococcus furiosus* DNA polymerase, and (exo-) Pyrococcus GB-D DNA polymerase.

In a further embodiment of the invention, a method of amplifying a polynucleotide sequence is provided. The method includes the steps of mixing a composition with a synthesis primer, and a synthesis template, with the composition including a first DNA polymerase possessing 3'-5' exonuclease activity, and a second DNA polymerase lacking 3'-5' exonuclease activity.

In yet another aspect of the invention, a method of amplifying a polynucleotide sequence is provided. The method includes the steps of mixing a composition with a synthesis primer, and a synthesis template, with the composition including a first DNA polymerase possessing 3'-5' exonuclease activity which is selected from the group consisting of *Pyrococcus furiosus* DNA polymerase, *Thermotoga maritima* DNA polymerase, *Thermococcus litoralis* DNA polymerase, and Pyrococcus GB-D DNA polymerase, and a second DNA polymerase lacking 3'5 exonuclease activity which is selected from the group consisting of *Thermus aquaticus* DNA polymerase, (exo-) *Thermococcus litoralis* DNA polymerase, (exo-) *Pyrococcus furiosus* DNA polymerase, and (exo-) Pyrococcus GB-D DNA polymerase.

Other objects and features will be in part apparent and in part pointed out hereinafter.

SUMMARY OF ABBREVIATIONS AND TERMS

The listed abbreviations and terms, as used herein, are defined as follows:

| Abbreviations: | |
|---|---|
| bp = | base pairs |
| kb = | kilobase; 1000 base pairs |
| nt = | nucleotides |
| EME = | beta-mercaptoethanol |
| $PP_i$ = | sodium pyrophosphate |

In use, the following 3-letter abbreviations often refer to the single-chain DNA polymerase elaborated by the microorganism.

| Pfu = | *Pyrococcus furiosus* |
|---|---|
| Pwo = | *Pyrococcus woesii* |
| Taq = | *Thermus aquaticus* |
| Tfl = | *Thermus flavus* |
| Tli = | *Thermococcus literalis* |

Klentaq-nnn=N-terminally deleted *Thermus aquaticus* DNA polymerase that starts with codon nnn+1, although that start codon and the next codon may not match the WT sequence because of alterations to the DNA sequence to produce a convenient restriction site.

| WT = | wild-type (full length) or deletion of only 3 aa |
|---|---|
| aa = | amino acid(s) |
| ST = | Stoffel fragment, an N-terminal | deletion of *Thermus aquaticus* DNA polymerase that could be named Klentaq-288.

-LA=Long and Accurate; an unbalanced mixture of two DNA polymerases, at least one lacking significant 3'-exonuclease activity and at least one exhibiting significant 3'-exonuclease activity.

| PCR = | (noun) 1. The Polymerase Chain |
|---|---|

Reaction
2. One such reaction/amplification experiment. 3. (verb) To amplify via the polymerase chain reaction.

| ul = | microliter(s) |
|---|---|
| ATCC = | American Type Culture Collection |
| Megaprimer = | double-stranded DNA PCR product used | as primer in a subsequent PCR stage of a multi-step procedure.

Deep Vent=DNA polymerase from *Pyrococcus* species GB-D; purified enzyme is available from New England Biolabs.

Deep Vent exo-=mutant form of Deep Vent DNA polymerase lacking 3'(editing)-exonuclease.

Vent=DNA polymerase from *Thermococcus litoralis*; purified enzyme is available from New England Biolabs.

Vent exo-=mutant form of Vent DNA polymerase lacking 3'(editing)-exonuclease.

Pfu=DNA polymerase from *Pyrococcus furiosus* lacking 3'(editing)-exonuclease; purified enzyme is available from Stratagene Cloning Systems, Inc.

Pfu exo-=mutant form of Pfu DNA polymerase purified enzyme is available from Stratagene Cloning Systems, Inc.

SEQUENASE=A chemically modified or a mutated form of phage T7 or T3 DNA polymerase wherein the modification or mutation eliminates the 3'-exonuclease activity.

THESIT=polyethylene glycol monododecyl ether.

BRIEF DESCRIPTION OF THE DRAWINGS

FIGS. 1(A-C) demonstrate the large increase in efficiency of large DNA span PCR achieved by variations of a preferred embodiment of the enzyme formulation of the invention. Although KlenTaq-278 or Pfu DNA polymerase, alone, are shown to catalyze a low level of 6.6 kb PCR product formation, various combinations of the two are seen to be much more efficient. Lower and lower amounts of Pfu in combination with Klentaq-278 are seen to be effective, down to the minimum presented, 1/640. Of those shown, only a combination of Klentaq-278 and Pfu can catalyze efficient amplification of 6.6 kb. Per 100 ul, the indicated level of each enzyme (see Methods, Example 7, for unit concentrations) was used to catalyze PCR reactions templated with 19 ng λplac5 DNA and primers MBL and MBR. 20 cycles of 94° 2 min., 60° 2 min., 72° 10 min.

FIG. 2 demonstrates the ability to amplify 8.4 kb, 12.5 kb, 15 kb, and 18 kb with high efficiency and large yield, utilizing the 1/640 ratio embodiment of the enzyme formulation of the invention. Target product size is indicated above each lane as kb:. Level of template per 100 ul is indicated as ng λ:. 20 or 30 cycles of PCR were each 2 sec. 94°, 11 min. 70°. These early amplifications were non-optimal in several respects compared to the current optimal procedure (see Methods, Example 7): thick-walled tubes were employed instead of thin, catalysis was by 1 ul KlentaqLA-64 (63:1:Klentaq-278:Pfu) instead of KlentaqLA-16, the 27mer primers were used (see Table 3) instead of longer primers, the extension/annealing temperature was 70° instead of 68°, and the Omnigene thermal cycler was used.

DESCRIPTION OF THE PREFERRED EMBODIMENT

Figure 1B:
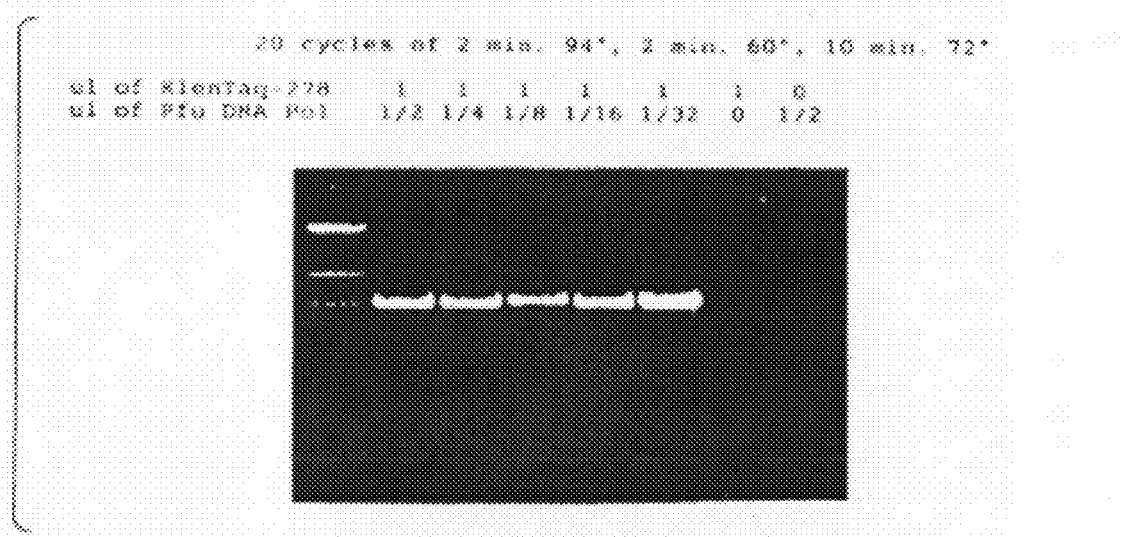
FIGS. 1(A-C) are depictions, respectively, of an agarose gel on which was loaded a portion of a test PCR experiment.

DNA polymerases such as those discussed in this application are commonly composed of up to three identifiable and separable domains of enzymatic activity, in the physical order from N-terminal to C-terminal, of 5'-exonuclease, 3'-exonuclease, DNA polymerase. Taq DNA polymerase has never had a 3'-exonuclease, but certain mutations of its N-terminal portion lead to a deletion of its 5'-exonuclease activity. Other DNA polymerases mentioned, such as Pfu DNA polymerase, do not have the 5'-exonuclease, but their 3'-exonuclease function is central to the aspect of the invention directed to mixtures of DNA polymerases E1 (lacking 3'-exonuclease activity) and E2 (having 3'-exonuclease activity). In these mixtures, the presence of 5'-exonuclease in either E1 or E2 has not been shown to be essential to the primary advantages of the present invention.

Table 1 below depicts the nucleotide sequence of primers that can be used for amplification of the gene for a preferred embodiment of the DNA polymerase lacking 3'-exonuclease activity (Klentaq-278) included as the primary component of the formulation of DNA polymerases of this invention. The bulk of the DNA sequence for the gene (between the primers) and the resultant amino acid sequence of the enzyme, is defined by the indicated GenBank entry.

TABLE 1

Primers that amplify the gene for KlenTaq-278

A. The primer at the 5' side of the target fragment.
The start codon is indicated with ***.

TABLE 1-continued

Primers that amplify the gene for KlenTaq-278

```
       NcoI  10          20          30          KT1 36MER
GAGCCATGGGCCTCCTCCACGAGTTCGGCCTTCTGG    (SEQ ID NO: 1)
      ***  |||||||||||||||||||||||||||
           m  g  L  L  H  E  F  G  L  L  E  ... <-- upper case are WT
aa
           278   280   282   284   286   288 <-- codon numbering for WT
aa
AGTTTGGCAGCCTCCTCCACGAGTTCGGCCTTCTGG . . . (SEQ ID NO: 14)
959        969       979          TaqPol.seq GenBank entry
Accession No. J04639 (numbering includes 5' non-translated
region)
```

B. The primer at the 3' side of the target fragment. The two stop codons are indicated with ***. To demonstrate the homology, the other (complementary) strand of the actual primer is shown here.

```
--other strand-- KLENTAQ32 35mer
                              HindIII
          26           16   ****** 6
GGACTGGCTCTCCGCCAAGGAGTAGTAAGCTTCGC (SEQ ID NO: 3)
|||||||||||||||||||||||||||   ||
   D  W  L  S  A  K  E  *
   826   828   830   832
GGACTGGCTCTCCGCCAAGGAGTGATACCACC (SEQ ID NO: 15)
      2604       2614       2624
TaqPol.seq
```

Table 2 below depicts the nucleotide sequence of the same primers as in Table 1, and shows that these same primers can be used for amplification of the analogous gene from *Thermus flavus*.

TABLE 2

The same primers as in Table 1 are homologous to *Thermus flavus* DNA.

```
           10          20          30
GAGCCATGGGCCTCCTCCACGAGTTCGGCCTTCTGG      KT1 36MER
      ***  |||||||||||||||||||||||| ||||
           m  g  L  L  H  E  F  G  L  L  E ...   <-- upper case are
WT aa
           278   280   282   284   286   288 <-- codon numbering for
WT aa
AGTTTGGAAGCCTCCTCCACGAGTTCGGCCTCCTGG      Tfl.seq GenBank
                                          entry
      1387      1397      1407            Accession number X66105
                (numbering includes 5' non-translated region)

26          16           6      --other strand--
GGACTGGCTCTCCGCCAAGGAGTAGTAAGCTTCGC       KLENTAQ32 35mer
|||||||||||||||||||||||||||    |  |  |
   D  W  L  S  A  K  E  *
   826   828   830
GGACTGGCTCTCCGCCAAGGAGTAGGGGGGTCCTG       Tfl.seq
      3032      3042      3052
```

Referring now to Table 1, the primers and logic for amplification by PCR of the recombinant DNA sequence encoding a preferred embodiment of the thermostable DNA polymerase of the invention lacking 3'-exonuclease activity (referred to herein as Klentaq-278), are set forth. As depicted in Table 1, an initiator methionine and a glycine residue occupy the first two N-terminal positions of Klentaq-278, previously occupied by residues 279 and 280 of WT *Thermus aquaticus* DNA polymerase, followed by the amino acid sequence of wild-type *Thermus aquaticus* DNA polymerase, beginning with the amino acid residue at position 281 as described by Lawyer et al. The codons encoding amino acid residues 1 through 280 of *Thermus aquaticus* DNA polymerase are therefore deleted, and the amino acids 1 thru 280 are not present in the resulting gene product.

The primers and logic for amplification of another preferred embodiment of the DNA polymerase of the invention lacking 3'-exonuclease activity are set forth in Table 2. In this embodiment, the same deletion mutation described above is made to the highly analogous enzyme *Thermus flavus* DNA polymerase.

The mutant DNA polymerase Klentaq-278 exhibits thermostability at temperatures above those reported for previous variants of *Thermus aquaticus* DNA polymerase and has demonstrated a fidelity in final PCR products which is greater than that of WT *Thermus aquaticus* DNA polymerase, when both are utilized at the 72° C. temperatures recommended for DNA synthesis.

A vector is also provided which includes a recombinant DNA sequence encoding a DNA polymerase comprising the amino acid sequence of *Thermus aquaticus* or *Thermus flavus*

DNA polymerase, except that it adds a methionine and glycine residue at the N-terminal and excludes the N-terminal 280 amino acids of wild-type *Thermus aquaticus* DNA polymerase (see Lawyer et al., supra).

In preferred embodiments, the vector is that nucleic acid present as plasmid pWB254b (SEQ ID NO:5) deposited as ATCC No. 69244 or a host cell containing such a vector.

In a related aspect, the invention features purified DNA polymerases of the type described herein. As used in this application, "purified" means that the polymerase of the invention is isolated from a majority of host cell proteins normally associated with it. Preferably, the polymerase is at least 10% (w/w) of the protein of a preparation. Even more preferably, it is provided as a homogeneous preparation, e.g., a homogeneous solution.

In general, the recombinant DNA sequence encoding for a preferred DNA polymerase lacking 3'-exonuclease activity which serves as the primary component of the DNA polymerase formulation of the present invention is amplified from a *Thermus aquaticus* genomic DNA or from a clone of the portion of the *Thermus aquaticus* DNA polymerase gene which is larger than the desired span, using the polymerase chain reaction (PCR, Saiki et al., Science 239:487, 1988), employing primers such as those in Table 1 into which appropriate restriction sites have been incorporated for subsequent digestion.

The recombinant DNA sequence described above is then cloned into an expression vector using procedures well known to those in this art. Specific nucleotide sequences in the vector are cleaved by site-specific restriction enzymes such as NcoI and HindIII. Then, after optional alkaline phosphatase treatment of the vector, the vector and target fragment are ligated together with the resulting insertion of the target codons in place adjacent to desired control and expression sequences. The particular vector employed will depend in part on the type of host cell chosen for use in gene expression. Typically, a host-compatible plasmid will be used containing genes for markers such as ampicillin or tetracycline resistance, and also containing suitable promoter and terminator sequences.

In a preferred procedure, the recombinant DNA expression sequence described above is cloned into plasmid pWB253 (expresses KlenTaq-235 deposited as ATCC No. 68431) or pWB250 (expresses luciferase/NPTII fusion), the backbone of which is pTAC2 (J. Majors, Washington University), a pBR322 derivative. The specific sequence of the resulting plasmid, designated pWB254b is SEQ ID NO: 5.

Bacteria, e.g., various strains of *E. coli*, and yeast, e.g., Baker's yeast, are most frequently used as host cells for expression of DNA polymerase, although techniques for using more complex cells are known. See, e.g., procedures for using plant cells described by Depicker, A., et al., *J. Mol. Appl. Gen.* (1982) 1:561. *E. coli* host strain X7029, wild-type F$^-$, having deletion X74 covering the lac operon is utilized in a preferred embodiment of the present invention.

A host cell is transformed using a protocol designed specifically for the particular host cell. For *E. coli*, a calcium treatment, Cohen, S. N., Proc. Natl. Acad. Sci. 69:2110 (1972), produces the transformation. Alternatively and more efficiently, electroporation of salt-free *E. coli* is performed after the method of Dower et al. (1988), Nucleic Acids Research 16:6127-6145. After transformation, the transformed hosts are selected from other bacteria based on characteristics acquired from the expression vector, such as ampicillin resistance, and then the transformed colonies of bacteria are further screened for the ability to give rise to high levels of isopropylthiogalactoside (IPTG)-induced thermostable DNA polymerase activity. Colonies of transformed *E. coli* are then grown in large quantity and expression of Klentaq-278 DNA polymerase is induced for isolation and purification.

Although a variety of purification techniques are known, all involve the steps of disruption of the *E. coli* cells, inactivation and removal of native proteins and precipitation of nucleic acids. The DNA polymerase is separated by taking advantage of such characteristics as its weight (centrifugation), size (dialysis, gel-filtration chromatography), or charge (ion-exchange chromatography). Generally, combinations of these techniques are employed together in the purification process. In a preferred process for purifying Klentaq-278 the *E. coli* cells are weakened using lysozyme and the cells are lysed and nearly all native proteins are denatured by heating the cell suspension rapidly to 80° C. and incubating at 80-81° C. for 20 minutes. The suspension is then cooled and centrifuged to precipitate the denatured proteins. The supernatant (containing Klentaq-278) then undergoes a high-salt polyethylene-imine treatment to precipitate nucleic acids. Centrifugation of the extract removes the nucleic acids. Chromatography, preferably on a heparin-agarose column, results in nearly pure enzyme. More detail of the isolation is set forth below in Example 3.

The novel DNA polymerase formulation of the present invention may be used in any process for which such an enzyme formulation may be advantageously employed. This enzyme formulation is particularly useful for PCR amplification techniques, but may also be used for other processes employing DNA polymerases such as nucleic acid sequencing, cycle sequencing, DNA restriction digest labelling and blunting, DNA labelling, in vivo DNA footprinting, and primer-directed mutagenesis.

Amplification

Polymerase chain reaction (PCR) is a method for rapidly amplifying specific segments of DNA, in geometric progression, up to a million fold or more. See, e.g., Mullis U.S. Pat. No. 4,683,202, which is incorporated herein by reference. The technique relies on repeated cycles of DNA polymerase-catalyzed extension from a pair of primers with homology to the 5' end and to the complement of the 3' end of the DNA segment to be amplified. A key step in the process is the heat denaturing of the DNA primer extension products from their templates to permit another round of amplification. The operable temperature range for the denaturing step generally ranges from about 93° C. to about 95° C., which irreversibly denatures most DNA polymerases, necessitating the addition of more polymerase after each denaturation cycle. However, no additional DNA polymerase needs to be added if thermostable DNA polymerases such as *Thermus aquaticus* DNA polymerase are used, since they are able to retain their activity at temperatures which denature double-stranded nucleic acids. As described in Example 4, below, Klentaq-278 has demonstrated the ability to survive meaningful repeated exposure to temperatures of 99° C., higher than for any previously known DNA polymerase.

Deposit

Strain pWB254b/X7029 was deposited with the American Type Culture Collection, Maryland, on Feb. 18, 1993 and assigned the number ATCC 69244. Applicant acknowledges his responsibility to replace this culture should it die before the end of the term of a patent issued hereon, 5 years after the last request for a culture, or 30 years, whichever is the longer, and his responsibility to notify the depository of the issuance of such a patent, at which time the deposits will be made available to the public. Until that time the deposits will be made available to the Commissioner of Patents under the terms of 37 C.F.R. Section 1-14 nad 35 U.S.C. §112.

In the principal aspect of the invention, a target length limitation to PCR amplification of DNA has been identified and addressed. Concomitantly, the base pair fidelity, the ability to use PCR products as primers, and the maximum yield of target fragment were increased. These improvements were achieved by the combination of a DNA polymerase lacking significant 3'-exonuclease activity, preferably, Klentaq-278 described above, with a low level of a DNA polymerase exhibiting significant 3'-exonuclease activity (for example, Pfu, Vent, or Deep Vent). Surprisingly, target fragments of at least 35 kb can be amplified to high yields from, for example, 1 ng lambda DNA template with this system.

Moreover, products in the range 6.6 to 8.4 kb can be efficiently amplified by a formulation of thermostable DNA polymerases consisting of a majority component comprised of at least one thermostable DNA polymerase lacking 3'-exonuclease activity and a minority component comprised of at least one thermostable DNA polymerase exhibiting 3'-exonuclease activity, i.e., wherein the ratio of DNA polymerase lacking 3'-exonuclease activity to that exhibiting 3'-exonuclease activity exceeds 1 to 1, measured by DNA polymerase activity units (or by weight where the DNA polymerase activity of the 3'-exonuclease activity-exhibiting enzyme has been eliminated, as described below).

The prior art technology only allowed relatively inefficient and sporadic amplification of fragments in this size range, resulting in only relatively faint product bands or no detectable product at all. In light of the current discovery, I believe I understand the reason for the inefficiency of the prior art. Without limiting myself to any particular theory, it is believed that *Thermus aquaticus* DNA polymerase and its variants are slow to extend a mismatched base pair (which they cannot remove since they lack any 3'-exonuclease). A couple of companies (New England Biolabs and Stratagene) have introduced thermostable enzymes which exhibit a 3'-(editing) exonuclease which should, one would think, allow the removal of mismatched bases to result in both efficient extension and more accurately copied products. In practice, these two enzymes (Vent and Pfu DNA polymerase) are unreliable and much less efficient than expected. One possible explanation for the unreliability of these enzymes for PCR is that the 3'-exonuclease often apparently attacks and partially degrades the primers so that little or no PCR is possible. This primer attack problem is worse for some primers than others. It has been reported (Anonymous, The NEB Transcript, New England Biolabs, (March, 1991) p. 4.) that the Vent DNA polymerase leaves the 5' 15 nt intact, so that if the annealing conditions allow that 15 nt to prime, PCR could presumably proceed. This would of course only allow annealling at lower, non-selective temperatures, and the 5' 15 nt of the primers must be exactly homologous to the template.

I have discovered that the beneficial effects of a 3'-exonuclease can be obtained with an unexpectedly minute presence of one or more DNA polymerases which exhibit 3'-exonuclease activity (herein called "E2") such as certain Archaebacterial DNA polymerases, whilst efficient extension is being catalyzed by a large amount of one or more DNA polymerases which lack 3'-exonuclease activity, such as Klentaq-278 or AT (herein called "E1"). As a minority component of a formulation or mixture of DNA polymerases, the unreliability and inefficiency of the 3'-exonuclease DNA polymerase, discussed above, is substantially reduced or eliminated. Moreover, since it is believed that the 3'-exonuclease is removing mismatches to eliminate pausing at the mismatches, the resulting DNA exhibits fewer base pair changes, which is a valuable decrease in the mutagenicity of PCR without sacrificing flexibility, specificity, and efficiency. In fact, the combination, even for KlenTaq-278/Pfu units ratios as high as 2000, exhibited greatly increased efficiency of amplification. For most applications, the mixture of DNA polymerases must be at a relative DNA polymerase unit ratio of E1 to E2 of at least about 4:1, before enhanced product length and yield can be achieved. When Pfu DNA polymerase was used in the formulation, the ratio preferably is in the range 80 to 1000 parts KlenTaq-278 per part (unit) Pfu, more preferably from about 150 to about 170:1, and most preferably, is about 160:1, depending somewhat on the primer-template combination. Similar ratios are preferred for mixtures of Pfu and Klentaq-291.

If Deep Vent is substituted for Pfu for use in combination with Klentaq-278 or -291, the most preferred ratios for most applications increases to from about 450 to about 500:1 E1 to E2; if full-length (WT) Taq or Amplitaq is included as E1, the most preferred ratio to Pfu or other E2 component is between about 10 and about 15:1 of E1 to E2.

E2 of the invention includes, but is not limited to, DNA polymerase encoded by genes from Pfu, Vent, Deep Vent, T7 coliphage, Tma, or a combination thereof. E1 of the invention includes, but is not limited to, a mutant, 3'-exonuclease negative form of an E2 DNA polymerase, or alternatively, a DNA polymerase which, in unmutated form, does not exhibit significant 3'-exonuclease activity, such as the DNA polymerases encoded by genes from Taq, Tfl, or Tth, or a combination thereof.

As discussed below, the formulation of DNA polymerases of the present invention also includes formulations of DNA polymerase wherein E1 comprises a reverse transcriptase such as SEQUENASE.

Additional examples of the formulations of the present invention include mixtures wherein E1 comprises or consists of a mutant or chemical modification of T7 or T3 DNA polymerase and E2 comprises or consists of a wild-type T7 or T3 DNA polymerase, or, in another variation, E1 comprises or consists of a Vent DNA polymerase lacking 3'-exonuclease activity (sold by New England Biolabs as Vent exo−) and E2 comprises or consists of Vent.

The principal here discovered, namely the use of low levels of 3' exonuclease during primer extension by a DNA polymerase lacking 3' exonuclease, is preferably employed using thermostable DNA polymerases, but is applicable to general DNA polymerase primer extensions, including normal temperature incubations (i.e. using non-thermostable DNA polymerases) and including reverse transcriptase enzymes, which are known to lack a 3'-(editing) exonuclease (Battula & Loeb, 1976). An example of the former is the use of SEQUENASE (exo-) as the majority enzyme, and wild-type T7 DNA polymerase (exo+) or Klenow fragment as the minority component. An example of the latter is AMV (Avian Myoblastosis Virus) or MLV (Murine Leukemia Virus) Reverse Transcriptase as the major component, and Klenow fragment, T7 DNA polymerase, or a thermostable DNA polymerase such as Pfu or Deep Vent as the minor component. Because of the lower activity of thermostable DNA polymerases at the temperatures of 37 degrees and 42 degrees used by these reverse transcriptases, higher levels are likely to be required than are used in PCR. Although Klenow fragment DNA polymerase is not a preferred DNA polymerase using RNA as a template, it does function to recognize this template (Karkas, 1973; Gulati, Kacian & Spiegelman, 1974), particularly in the presence of added Mn ion. Added Mn ion is routinely used to achieve reverse transcription by thermostable DNA polymerase Tth, unfortunately (in the prior art) without the benefit of an exo+ component. It must be stressed that for the use of the exo+ component for reverse transcriptase reactions, extra care must be taken to ensure that the exo+ component is entirely free of contaminating RNAse.

The following references describe methods known in the art for using reverse transcriptases, and are hereby incorporated by reference.

Battula N. Loeb L A. On the fidelity of DNA replication. Lack of exodeoxyribonuclease activity and error-correcting function in avian myeloblastosis virus DNA polymerase. *Journal of Biological Chemistry.* 251(4):982-6, Feb. 25, 1976.

Gulati S C. Kacian D L. Spiegelman S. Conditions for using DNA polymerase I as an RNA-dependent DNA polymerase. *Proceedings of the National Academy of Sciences of the United States of America.* 71(4):1035-9, April 1974.

Karkas J D. Reverse transcription by *Escherichia coli* DNA polymerase I. *Proc Natl Acad Sci U S A.* 70(12):3834-8, December 1973.

DNA Polymerase with No Polymerase Activity, Only 3'-exonuclease Activity:

While not limiting myself to a particular theory, applicant believes that the enzymatic activity of value in the minor (E2) component is the 3'-exonuclease activity, not the DNA polymerase activity. In fact, it is further believed that this DNA polymerase activity is potentially troublesome, leading to unwanted synthesis or less accurate synthesis under conditions optimized for the majority (E1) DNA polymerase component, not the minority one. As taught by [Bernad, Blanco and Salas (1990) Site-directed mutagenesis of the YCDTDS amino acid motif of the phi 29 DNA polymerase, *Gene* 94:45-51.] who mutated the "Region I" DNA conserved DNA polymerase motif of phi 29 DNA polymerase, either Region III or Region I of the Pfu DNA polymerase gene are mutated, which has been sequenced by Uemori, T., Ishino, Y., Toh, H., Asada, F. and Kato, I. Organization and nucleotide sequence of the DNA polymerase gene from the archaeon Pyrococcus furiosus, *Nucleic Acids Res.* 21, 259-265 (1993).

The following examples illustrate the invention.

EXAMPLE 1

Construction of an Expressible Gene for Klentaq-278

In order to construct the Klentaq-278 DNA polymerase gene having a recombinant DNA sequence as described above, the following procedure was followed.

The mutated gene was amplified from 0.25 ug of total *Thermus aquaticus* DNA using the polymerase chain reaction (PCR, Saiki et al., Science 239:487, 1988) primed by the two synthetic DNA primers of Table 1. Primer KT1, SEQ ID NO:1, has homology to the wild-type DNA starting at codon 280; this primer is designed to incorporate a NcoI site into the product amplified DNA. Primer Klentaq32, SEQ ID NO:3, a 33mer spanning the stop codon on the other strand of the wild-type gene encoding *Thermus aquaticus* DNA polymerase, and incorporating a HindIII site and a double stop codon into the product DNA.

The buffer for the PCR reaction was 20 mM Tris HCl pH 8.55, 2.5 mM $MgCl_2$, 16 mM $(NH_4)_2SO_4$, 150 ug/ml BSA, and 200 uM each dNTP. The cycle parameters were 2' 95°, 2' 65°, 5' 72°.

In order to minimize the mutations introduced by PCR (Saiki et al., supra), only 16 cycles of PCR were performed before phenol extraction, ethanol precipitation, and digestion with the restriction enzymes NcoI and HindIII.

EXAMPLE 2

Preparation of an Expression Vector

The product NcoI and HindIII fragment was cloned into plasmid pWB254b which had been digested with NcoI, HindIII, and calf intestine alkaline phosphatase. The backbone of this plasmid, previously designated pTAC2 and obtained from J. Majors, carries the following elements in counter-clockwise direction from the PvuII site of pBR322 (an apostrophe ' designates that the direction of expression is clockwise instead of counter clockwise): a partial lacZ', sequence, lacI', lacPUV5 (orientation not known), two copies of the tac promoter from PL Biochemicals Pharmacia-LKB; catalog no. 27-4883), the T7 gene 10 promoter and start codon modified to consist of a NcoI site, a HindIII site, the trpA terminator (PL no. 27-4884-01), an M13 origin of replication, and the $Amp^R$ gene of pBR322. Expression of the cloned gene is expected to be induced by 0.1 mM IPTG.

Ampicillin-resistant colonies arising from the cloning were assayed by the single colony thermostable DNA polymerase assay of Sagner et al. (1991) [GENE 97:119-23] and 4 strong positives were sized by the toothpick assay (Barnes, Science 195:393, 1977). One of these, number 254.7, was of the expected size except for a small proportion of double insert. This plasmid was further purified by electroporation into *E. coli* X7029 and screened for size by the toothpick assay, and one plasmid of the expected size with no double insert contamination was designated pWB254b. This plasmid was used for the production of Klentaq-278 described herein.

EXAMPLE 3

Purification of Large Amounts of Klentaq-278

Plasmid pWB254 has a double (tandem repeat) tac promoter and the T7 gene 10 leader sequence, an ATG start codon, a glycine codon and then codons 280-832 of *Thermus aquaticus* DNA polymerase, then a tandem pair of stop codons followed by the trp transcription terminator. The pBR322-based plasmid vector (pTac2 from John Majors) is ampicillin resistant. The cells are grown on very rich medium (see below). Bacterial host X7029 is wild-type $F^-$ *E. coli* except for deletion X74 of the lac operon.

Medium: Per liter water, 100 mg ticarcillin (added when cool), 10 g Y.E., 25 g. Tryptone, 10 g. glucose, 1XM9 salts with no NaCl (42 mM $Na_2PO_4$, 22 mM $KH_2PO_4$, 19 mM $NH_4Cl$). Do not autoclave the glucose and the 10XM9 together; instead, autoclave one of them separately and mix in later. Adjust pH to 8 with 5 M NaOH (about 1 ml). Add IPTG to 0.1 mM at $OD_{550}=1$ or 2, and shake well at 30° C. From OD=2 up to 8 or 10, every half hour or so do the following:

1. Read the pH with pH sticks 5-10. Adjust to pH 8.5 with 5 M NaOH and swirling (2 to 5 ml per liter) whenever the pH falls below 8.

2. Read and record the $OD_{550}$, usually as a 1/10 or 1/50 dilution.

3. This addition of glucose is optional and not necessarily of any value (evaluation of this question is incomplete at this time.) Read the glucose level with glucose sticks, and add an additional 0.5% (10 ml of 50%) if the level falls below 0.2%.

If it is late, the cells can shake at 30° C. all night after the last pH adjustment. Alternatively, set them in the cold room if they have not grown much in a few hours.

Concentrate the cells e.g. by centrifugation in a GS3 rotor for 8 minutes at 8 krpm. Pour off the supernatant and add culture to spin more down onto the same pellets.

Lysis:

Resuspend the cells in milliliters of TMN buffer equal to twice the packed cell weight in grams: (50 mM Tris-HCl pH 8.55, 10 mM $MgCl_2$, 16 mM $(NH_4)_2SO_4$)

To each 300 ml of cell suspension add 60 mg lysozyme and incubate the cells at 5-10° C. with occasional swirling for 15 minutes. Then add NP40 or Triton X100 to 0.1%, and Tween 20 to 0.1%, by adding 1/100 volume of a solution of 10% in each. Then heat the cell suspension rapidly to 80° C. by swirling it in a boiling water bath, then maintain the cells (fast becoming an extract) at 80-81° C. for 20 minutes. Use a clean thermometer in the cells to measure temperature. Be sure the flask and bath are covered, so that even the lip of the flask gets the full heat treatment. After this treatment, which is expected to have inactivated all but a handful of enzymes, cool the extract to 37° C. or lower in an ice bath and add 2 ml of protease inhibitor (100 mM PMSF in isopropanol). From this point forward, try not to contact the preparation with any flask, stir bar, or other object or solution that has not been autoclaved. (Detergents and BME are not autoclavable. The PEI and ammonium sulfate are also not autoclaved.) The purpose of the autoclaving is not only to avoid microbial contamination, but also to avoid contamination with DNA or nucleases.

Distribute into centrifuge bottles and centrifuge at 2° C. (for instance, 30 minutes at 15 krpm in a Sorval SS-34 rotor or 14 h at 4 krpm in a GS3 rotor). The supernatant is designated fraction I, and can be assayed for DNA polymerase activity.

High-Salt PEI Precipitation

After rendering fraction I 0.25 M in NaCl (add 14.6 g per liter), add five percent Polymin-P (PEI, polyethylene-imine, Sigma) dropwise with stirring on ice to precipitate nucleic acids. To determine that adequate Polymin-P has been added, and to avoid addition of more than the minimum amount necessary, test ½ ml of centrifuged extract by adding a drop of Polymin-P, and only if more precipitate forms, add more Polymin-P to the bulk extract, mix and retest. Put the test aliquots of extract back into the bulk without contaminating it.

To confirm that enough PEI has been added, centrifuge 3 ml and aliquot the supernatant into ½ ml aliquots. Add 0, 2, 4, 6 or 10 ul of 5% PEI. Shake, let sit on ice, and centrifuge in the cold. Load 15 ul of these aliquot supernatants onto an agarose gel containing ethidium bromide and electrophorese until the blue dye has travelled 2 cm. Inspect the gel on a UV light box for detectable DNA or RNA in the supernatant. For the bulk extract, use about 1/100 volume (i.e. 2-3 ml for a 300 ml extract) excess 5% PEI over the minimum necessary to remove all DNA by the agarose gel test.

Stir in the cold for at least 15 minutes. Centrifugation of the extract then removes most of the nucleic acids. Keep the supernatant, avoiding any trace of the pellet.

Dilute the PEI supernatant with KTA buffer until the conductivity is reduced to at or below the conductivity of KTA buffer with added 22 mM ammonium sulfate. (Check conductivity of 1/40 dilution compared to similar dilution of genuine 22 mM A.S. in KTA.) Usually this is about a 5-fold dilution.

Chromatography with Bio-Rex 70 (used by Joyce & Grindley) (Joyce, C. M. & Grindley, N. D. E. (1983) Construction of a plasmid that overproduces the large proteolytic fragment (Klenow fragment) of DNA polymerase I of *E. coli*, Proc. Natl. Acad. Sci. U.S.A. 80, 1830-1834) is unsuccessful (no binding), but unavoidable, since without it, the next column (heparin agarose) will not work efficiently. I believe that the important function of the Bio-Rex 70 step is to remove all excess PEI, although it is possible that some protein is removed as well. CM-cellulose does not substitute for Bio-Rex 70.

Pass the diluted PEI supernatant through equilibrated Bio-Rex 70 (10 ml per 100 g. cells). The polymerase activity flows through. Rinse the column with 2 column volumes of 22 mM A.S./KTA. Our procedure is to set up the following heparin agarose column so that the effluent from the Bio-REX 70 column flows directly onto it.

Heparin Agarose Chromatography (room temperature, but put fractions on ice as they come off.)

Load the Bio-Rex flow-through slowly onto heparin agarose (Sigma; 10 ml per 100 grams of cells [this could be too little heparin agarose].) Wash with several column volumes of KTA+22 mM A.S., then three column volumes of KTA+63% glycerol+11 mM A.S., then elute the pure enzyme with KTA+ 63% glycerol+222 mM A.S.+0.5% THESIT (this is more THESIT for the final eluate.) Pool the peak of polymerase activity or $OD_{280}$/(starts about at ⅔ of one column volume after 222 mM starts, and is about 2 column volumes wide). Store pool at −20° C.

The storage buffer is a hybrid of, and a slight variation of, AmpliTaq storage buffer as recommended by Perkin-Elmer Cetus and Taq storage buffer used by Boehringer-Mannheim: 50% glycerol (v/v; 63% w/v), 222 mM ammonium sulfate (diluted to about 50 mM for bench-strength samples), 20 mM Tris-HCl pH 8.55,0.1 mM EDTA, 10 mM mercaptoethanol, 0.5% THESIT.

The THESIT causes some thickening and cloudiness below −10° C. This seems to cause no harm, but we suggest you warm the enzyme to 0° C. on ice before aliquoting for use. THESIT replaces the combination of 0.5% Triton-X100, 0.5% Tween 20, which you may want to consider as an alternative.

I have had sporadic reports that freezing can inactivate the enzyme. Exercise caution in this regard. This question is under current investigation. Storage at −80° (after quick-cooling with liquid nitrogen) is being tested and looks promising, but more than one freeze-thaw cycle has been deleterious to the enzyme preparation on some occasions.

Our final yield of enzyme from 7 liters (100 g cells) was once 28 ml at a concentration of 120,000 units per ml (4× bench-strength).

¼ ul of bench-strength enzyme will support the PCR of a 2 kb span of DNA in a 100 ul reaction. Template is 5-10 ng of plasmid DNA. Each cycle consists of 1 min 98° C., 1 min 65° C., 6 min 72° C. Cycle number is 16-20. Less enzyme is needed for smaller-sized products (⅛ ul for 500 bp) and more enzyme is needed for larger products (1 ul for 5 kb).

| KTA Buffer | per liter |
|---|---|
| 20 mM Tris 8.55 | 10 ml of 2M |
| 10 mM BME | 0.7 ml neat |
| 10% w/v Glycerol | 100 g. |
| 0.1 mM EDTA | 0.2 ml of .5M |
| 0.1% w/v THESIT | 10 ml of 10% |

Rough Incorporation Assay

1 X PC2 Buffer (20 mM Tris-HCl pH 8.55, 2.5 mM $MgCl_2$, 16 mM $(NH_4)_2SO_4$, 100 ug/ml BSA)

200-250 ug/ml activated salmon sperm DNA 40 uM each dNTP+10-50 uCi $\alpha$-$^{32}$P-DATP per ml To 25 ul assay mix on ice add 0.2 ul of enzyme fraction, undiluted, or diluted in 8 ul of 1XPC2 buffer (or a 1/5 or 1/25 dilution thereof.) Prepare standard Klentaq or Amplitaq, zero enzyme and total input samples, also. Incubate 10 min. at 72° C., then chill. Spot 5 or 8 ul onto filter paper and wash twice for 5-10 min. with 5% TCA, 1% $PP_i$. If pieces of paper were used, count each using Cerenkov radiation or hand monitor. If a single piece of 3 MM paper was used, autoradiograph for 60'.

PCR Assay to Give 2 kb Product.

Make up 1 ml of PCR reaction containing 50 ng of plasmid pLc (a clone of an R color control cDNA from maize. PNAS 86:7092; Science 247:449), 200 pmoles each of primers Lc5 (SEQ ID NO:11) and Lc3 (SEQ ID NO:12), PC2 buffer and 200 uM dNTPs, but no enzyme.

Distribute 100 ul into tube one, and 50 ul into the rest of 8-10 tubes. Add 1 ul of final pool of KlenTaq to tube one and mix. Then remove 50 ul to tube two and mix that, and so on down the series, which will then contain decreasing amounts of enzyme in two-fold steps. Cover each 50 ul reaction with a drop of mineral oil, spin, and PCR 16 cycles at 2' 95° C., 2' 65° C., 5' 72° C.

Final Bench-Strength KlenTaq-278 Enzyme

Using 63% glycerol/KTA (0.5% THESIT) buffer with 222 mM ammonium sulfate, dilute the pool conservatively so that ¼ ul should easily catalyze the amplification the 2 kb span by PCR. Do not decrease the ammonium sulfate concentration below 50 mM. Store at −20° C.

EXAMPLE 4

A PCR amplification assay to produce 2 kb of DNA product was conducted using *Thermus aquaticus* DNA polymerase (AmpliTaq) and Klentaq-278. To test polymerase thermostability at elevated temperatures, the DNA denaturation step of the PCR amplification reactions were conducted for 2 min. at 97° C., 98° C. and 99° C., respectively, using graduated concentrations of DNA polymerase.

The amplification procedures used followed approximately the protocol for amplifying nucleic acid sequences outlined by Saiki et al., Science 239:487, 1988. A 1 ml reaction mixture was prepared containing 100 ng of plasmid pLC, 200 pmoles each of primers Lc5 (SEQ ID NO:11) and Lc3 (SEQ ID NO:12), reaction buffer (20 mM Tris-HCl pH 8.55, 16 mM ammonium sulfate, 2.5 MM $MgCl_2$ and 150 ug/ml BSA), 200 uM dNTPs, but no enzyme. 100 ul of the reaction mixture was placed into tubes. Aliquots of AmpliTaq and Klentaq-278 were then added and 20 cycles of PCR were undertaken.

A range of enzyme concentrations was used in order to be able to detect small effects on the effective PCR catalysis activity. The template was 10 ng of pLc (a clone of an R color control cDNA from maize. PNAS 86:7092, Science 247:449). The primers were Lc5 (SEQ ID NO:11) and Lc3 (SEQ ID NO:12).

As a result of this experiment it was seen that 98° C. was not detectably detrimental to KlenTaq-278, yet AT was nearly completely inactivated by this temperature.

EXAMPLE 5

Efficient and Accurate PCR Amplification of Long DNA Targets: (Part A)

A preferred embodiment of the above formulation (designated KlenTaq-LA) is provided as follows: Starting with the purified enzymes in storage buffer, mix 1 ul of Pfu DNA polymerase at 2.5 u./ul with 64 ul of KlenTaq-278 at 25 u./ul. Store at −20° C.

Larger amounts of Pfu are detrimental to some PCR amplifications, perform equally for some, and are beneficial for some. For testing of the optimum level of Pfu, several reactions complete with KlenTaq-278 are aliquoted in the amount left to right of 75 ul, 25 ul, 25 ul, and as many additional 25 ul aliquots as desired. Then ⅜ ul of Pfu (equivalent to 0.5 ul per 100 ul—this is about the most that one would ever want) is added to the leftmost, 75 ul reaction and mixed. Serial, two-fold dilutions are then made as 25 ul+25 ul left to right along the row of tubes, adding no Pfu to the last one, as a control of KlenTaq-278 alone. A reaction of ½ or 1 ul (per 100 ul) of Pfu alone should also be run.

Reaction buffer is PC2 as above, supplemented with 200 uM of each dNTP and 800 uM of $MgCl_2$ (total $Mg^{++}$3.3 mM), and per 100 ul of reaction volume, 20 pmoles of each primer MBL (SEQ ID NO:7) and MBR (SEQ ID NO:8), and 30 ng of λplac5 intact phage. Per 100 ul of reaction volume, 1 or ½ ul of KTLA are effective levels of enzyme. Suitable PCR cycling conditions are two-temperature: 20 seconds at 94° C., 11 minutes at 70° C., for 20 cycles. Alternate cycling conditions include two-temperature PCR with 1 minute at 98° C. and 10 minutes at 65° C. 10 to 16 ul are loaded onto an agarose gel for product analysis by staining with ethidium bromide. See FIG. 1 for other details and variations. The template was λplac5, which carries a portion of the lac operon region of the *E. coli* genome. Thirty ng of phage DNA were included in each 100 ul of reaction volume, introduced as intact phage particles. The primers are homologous to wild-type lambda DNA and amplify λ DNA, not the lac DNA. Primer MBL No. 8757 (5' nucleotide matches base pair 27914 of λ DNA) is GCT TAT CTG CTT CTC ATA GAG TCT TGC (SEQ ID NO:7). Primer MBR No. 8835 (5' nucleotide matches bp 34570 of λ DNA) is ATA ACG ATC ATA TAC ATG GTT CTC TCC (SEQ ID NO:8). The size of the amplified product is therefore predicted to be 6657 bp.

As shown in FIG. 1A and 1B, each DNA polymerase enzyme (KlenTaq-278 or Pfu) alone gives rise to a faint product band (except for some reactions, when Pfu alone does not work at all), but the combinations all give rise to product bands that are 20 to 50 times more intense than either enzyme can catalyze on its own.

Figure 1C:
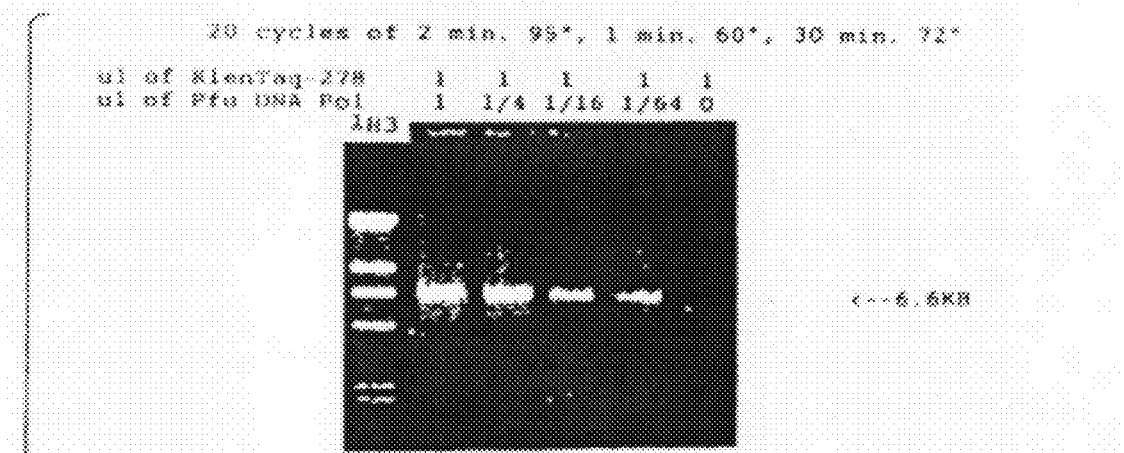

FIG. 1C, second lane from the right, shows the surprising result of adding as little as 1/64 ul of Pfu to 1 ul of KlenTaq-278 (a units ratio of 1/640). Not shown are data that as little as 1/200 ul (1/2000 in units) of Pfu contributed a noticeable improvement to the efficiency of this test amplification.

Vent DNA polymerase required 10-fold higher amounts (yet still minority amounts) for similar functionality.

An additional, beneficial, and unexpected attribute to the PCR reactions catalyzed by KlenTaq-LA was a phenomenal, never previously observed intensity and sharpness to the PCR product bands. In part, this increased yield is manifested by a dark area in the middle of the bands as photographed. This darker area in the ethidium flourescence is believed to be due to UV absorbance by the outside portions of the band, reducing the potential UV-activated flourescence. The system apparently allowed a much greater yield of product then did the prior art, which tended to create a broad smear of product, and increasing amounts of side product, when amplification was allowed to proceed to this extent.

EXAMPLE 6

Efficient and Accurate PCR Amplification of Long DNA Targets: (Part B)

Figure 2:
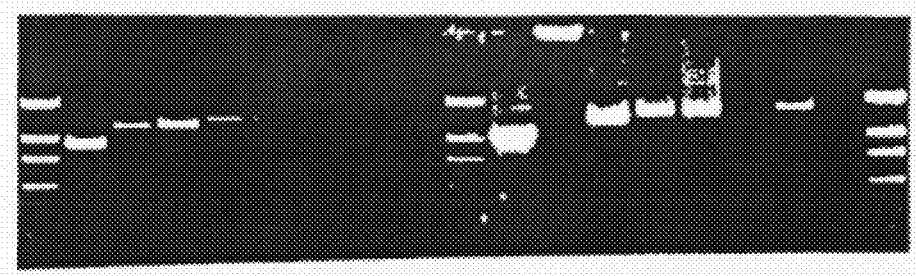
FIG. 2 is a depiction of an agarose gel on which were analyzed the products of PCR experiments to test the performance of an embodiment of the invention in catalyzing the amplification of fragments even longer than 6.6 kb.
Figure 2:
Figure 3:
FIG. 3 is a depiction of an agarose gel of a PCR amplification attempted using a 384 bp megaprimer (double-stranded PCR product) paired with a 43-mer oligonucleotide primer BtV5. Per 100 ul of reaction volume, the following enzymes (see Ex. 7, Methods, for unit concentrations) were used to catalyze amplifications: lane 1, 1 ul Pfu DNA polymerase; lane 2, 1/16 ul Pfu; lane 3, 1 ul Klentaq-278; lane 4, both enzymes together (1 ul Klentaq-278+1/16 ul Pfu). The 384 bp band near the bottom of the gel is the megaprimer, which was originally amplified using Klentaq-278. λH3=lambda DNA digested with HindIII. The only successful amplification resulted from the combination of the two enzymes (lane 4). Vent DNA polymerase could substitute for Pfu with the same result (data not shown).
Figure 3:
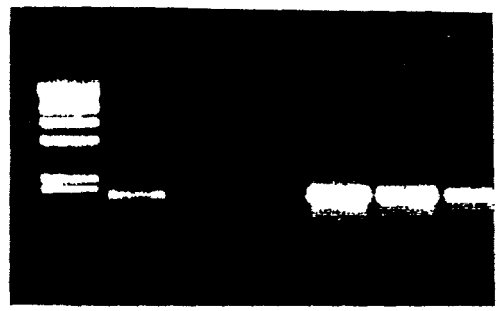
Figure 3:
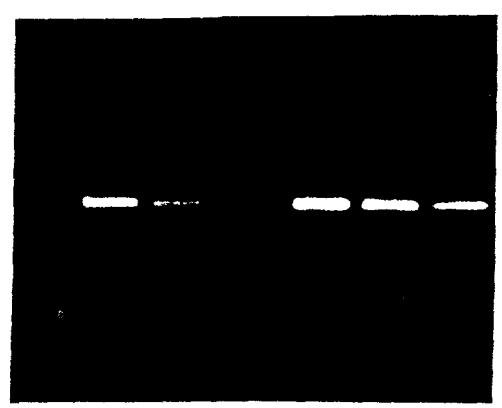

Efficient amplification of 8.4 kb, 12.5 kb, 15 kb, and 18 kb was demonstrated by the experiment depicted in FIG. 2. This experiment extended the demonstrated performance of the a preferred embodiment of the invention, 1/640 KlenTaq-LA, even further. The amplification was highly successful for the size range 8.4 to 15 kb, detectably successful for 18 kb, but not successful for an attempted 19.7 kb.

Eight different PCR reactions were run in this experiment, differing from each other in the template or amount of template or in the primer pair employed, as shown in the legend on FIG. 2. Each reaction was divided 3 ways and cycled differently in parts A, B, and C. Between parts A and B, this experiment compared 20 cycles to 30 cycles at 94° denaturation phase. In parts B and C, this experiment compared 94° to 93° for 30 cycles. This experiment utilized 1.3 ul of Klentaq-LA (at a Klentaq-278/Pfu ratio of 640) per 100 ul of reaction. This may have been a little too much enzyme, since high enzyme has been associated in previous experiments with the catastrophic synthesis of product which cannot enter the gel, as occurred here for the reaction products in channels 2B and 6C. At the current stage of development of long PCR using the invention, this poor outcome occurs about 10% of the time.

Comparing conditions B and C, it is apparent that a somewhat lower denaturation temperature is desirable. This is consistent with similar experiments comparing time at 94° C., in which yield of long PCR products was found to be decreased as the denaturation time increased in the order 2, 20, 60, and 180 seconds at 94° C. for the denaturation step of each cycle. These data indicate that there was at least one weak link, i.e. least thermostable component, in the reactions which is subject to inactivation at 94°. Since 94° is below the temperature known to damage the DNA polymerase activity and the DNA, it is believed that it is not the thermolabile element. In an alternative embodiment of this aspect of the invention Pfu DNA polymerase is replaced as the minority component with a more thermostable 3'-exonuclease of a DNA polymerase such as, but not limited to, that from the Archaebacterium strain ES4, which can grow at temperatures up to 114° C. [Pledger, R. J. and Baross, J. A., J. Gen. Microbiol. 137 (1991)], which maximum growth temperature exceeds that of the source of the Pfu DNA polymerase (103° C.; Blumentals, I. I. et al. (1990) Annals of the N.Y. Acad. Sci. 589:301-314.)

In the experiment in FIG. 2 the final intensity of the 15 kb band matched in only 20 cycles the yield obtained by Kainze et al.supra in 30 cycles for a band of similar size and from similar λDNA template amounts. This was a measure of the improved efficiency provided by the invention, and the further result was that the yield catalyzed by the invention in 30 cycles greatly exceeded the yield reported by these authors for 30 cycles. Accurate quantitation has not yet been carried out to measure the efficiency of the two methods, but inspection of FIG. 2 compared to the figure published by Kainze et al. shows a yield for the 15 kb fragment that is estimated to be some 100 times higher. This corresponds approximately to a doubled efficiency of PCR extension.

EXAMPLE 7

Efficent and Accurate PCR Amplification of Long DNA Targets: (Part C)

Materials and Methods

DNA Polymerases. DNA polymerases Vent and Deep Vent were supplied by New England Biolabs. Pfu DNA polymerase and its exo⁻ mutant were supplied by Stratagene at 2.5 units/ul. Klentaq-278 is an N-terminal deletion variant of Taq DNA polymerase as described above. Purified Klentaq-278 was as supplied by Ab Peptides, St. Louis, MO, USA at 25-35 units/ul (a protein concentration of about 0.7 ug/ul). One unit of DNA polymerase activity incorporates 10 nmoles of nucleotide in 30 min. at 72° C., utilizing activated (partially degraded) calf thymus DNA as template. Since activated calf thymus DNA is a somewhat undefined substrate and is structurally different from PCR reaction substrate, this assay was routinely eschewed in favor of a PCR-based assay to set the above stock concentration of Klentaq-278: the concentration of Klentaq-278 stock was adjusted so that 0.25 ul effectively (but 0.12 ul less effectively) catalyzes the amplification of a 2 kb target span from 10 ng of plasmid substrate with cycling conditions including 7 min. of annealing/extension at 65°. The mixture of $^{15}/_{16}$ ul Klentaq-278+$^{1}/_{16}$ ul Pfu DNA polymerases is designated KlentaqLA-16.

Figure 5:
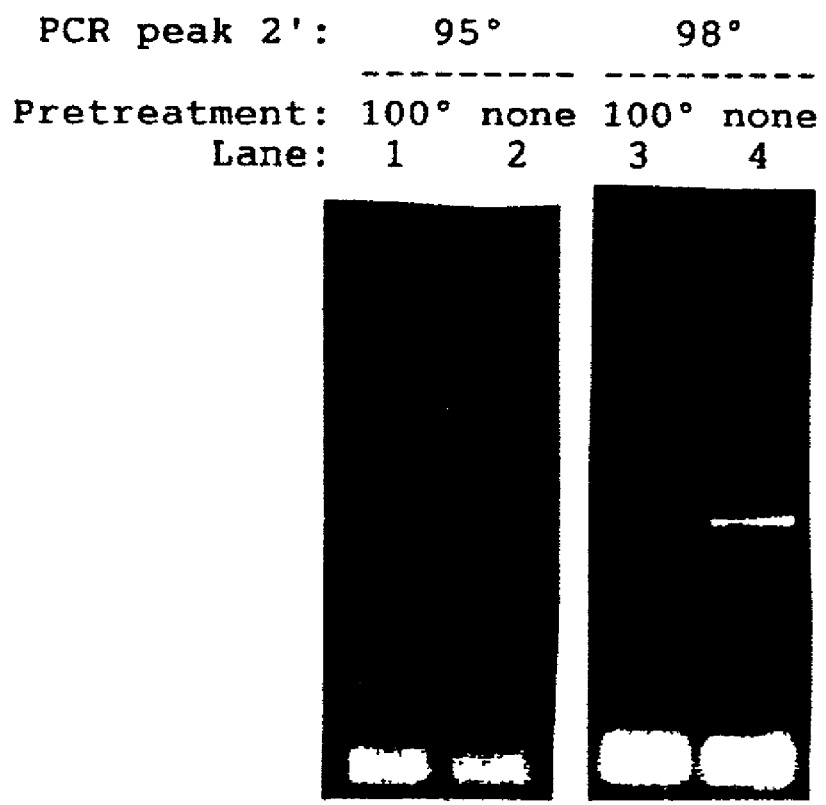
FIG. 5 is a depiction of an agarose gel showing a CHEF pulse-field analysis (ref. 11, 4 sec. switching time) of large PCR products amplified by KlentaqLA-16 (1.2 ul) under conditions which were suboptimal with respect to pH (unmodified PC2 buffer was used) and thermal cycler (Omnigene). Starting template (see Table 3) was at 0.1 ng/ul and the time at 68° in each cycle was 21 min. for products over 20 kb, 13 min. for lanes 4 & 5, and 11 min. for lanes 11-14. The volumes of PCR reaction product loaded were adjusted to result in approximately equal intensity; in ul: 12,12,4,2; 10,10,10; 2,2,4,1. The standard size lanes (S) show full-length λplac5 DNA (48645 bp) mixed with a HindIII digest of λ DNA. As for Table 1, the sizes in 5 figures are in base pairs, as predicted from the primer positions on the sequence of λplac5 DNA, and sizes with decimal points are in kb, as determined from this gel.
Figure 6A:
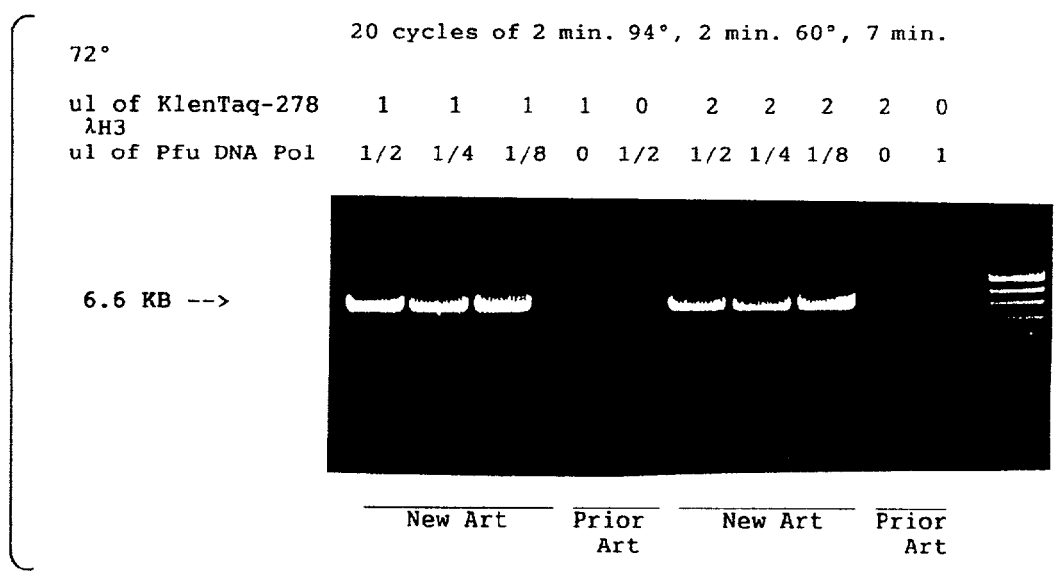
FIG. 6 is a depiction of an agarose gel of 28 kb and 35 kb products without (lanes 2,3) and with (lanes 5,6) digestion by restriction enzyme HindIII. Before HindIII digestion, the 28 kb product was amplified with 21 min. extension time per cycle, and the 35 kb product was cycled with 24 min. extension times, both in the RoboCycler at optimum pH (see Ex. 7, Methods). Lanes S (1,4,7) contain markers of undigested λplac5 and HindIII-digested λplac5 DNA.
Figure 6B:
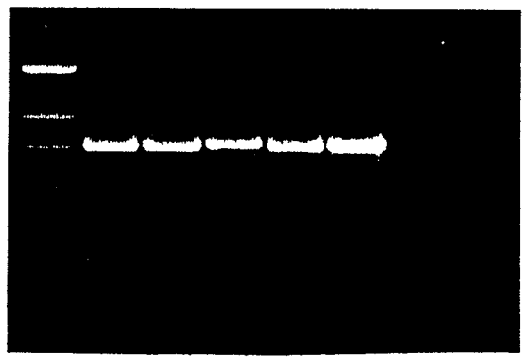
Figure 6C:
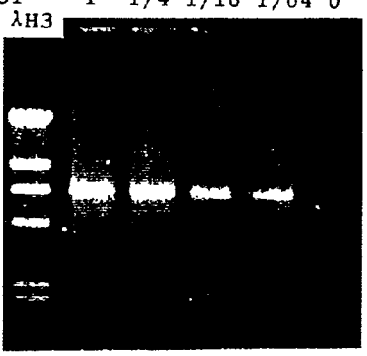

Agarose gel electrophoresis employed 0.7% to 1% agarose in 1XGGB (TEA) buffer [40 mM Tris acetate pH 8.3, 20 mM sodium acetate, 0.2 mM EDTA] at 2-3 v/cm, with 3% ficoll instead of glycerol in the loading dye. FIG. 5 employed 1% agarose pulsed-field CHEF (11) with a switching time of 4 sec. Standard DNA fragment sizes in every figure are, in kilobases (kb): 23.1, 9.4, 6.6, 4.4, 2.3, 2.0, and 0.56. FIG. 5 and 6 also have a full-length λplac5 standard band, 48645 bp.

All agarose gels were run or stained in ethidium bromide at 0.5 ug/ml and photographed (35 mm ASA 400 black and white film) or videographed (Alpha Innotech or Stratagene Eagle Eye) under UV illumination. While printing the gel photographs, the left halves of FIGS. 2 and 4 were exposed 50% less than the right halves.

DNA primers are listed in Table 3 and in the Sequence Listing.

Lambda DNA Templates. λvacA, a gift from S. Phadnis, is a λEMBL4-vectored clone of the cytotoxin gene region of *Helicobacter pylori* DNA. This DNA was extracted and stored frozen. The other phage template DNAs λplac5 (12) and λK138 (13) were added as intact phage particles that had been purified by CsCl equlibrium centrifugation, dialyzed, and diluted in 1× PC2 buffer.

Long and Accurate PCR. PC2 Reaction buffer (10) consisted of 20 mM Tris-HCl pH 8.55 at 25°, 150 ug/ml BSA, 16 mM $(NH_4)_2SO_4$, 3.5 mM $MgCl_2$, 250 uM each DNTP. For success above 28 kb (at 35 kb), 1.5 ul of 2 M Tris base was added to each reaction, corresponding to pH 9.1 measured for the Tris-HCl component only at 20 mM in water at 25° C. Contact with a pH probe was detrimental to the reactions, so pH was only measured on separate aliquots, and found to be 8.76 in the final reaction at 25° C. Each 100 ul of reaction volume contained 20 pmoles of each primer, and 0.1 to 10 ng of phage DNA template. 0.8 or 1.2 ul of KlentaqLA-16 was appropriate for under 20 kb and over 20 kb, respectively. Reaction volumes per tube were 33-50 ul, under 40 ul of mineral oil in thin-walled (PGC or Stratagene) plastic test tubes.

PCR reactions utilizing the primers at the ends of λ required a preincubation of 5 min. at 68°-72° to disrupt the phage particles and to allow fill-in of the λ sticky ends to complete the primer homology. Optimal cycling conditions were in a multiple-block instrument (Robo Cycler, Stratagene) programmed per cycle to 30 sec. 99°, 30 sec. 67°, and 11 to 24 min. at 68°, depending on target length over the range shown in Table 3. The second-best cycler was the Omnigene (HybAid), programmed under tube control per cycle to 2 sec. at 95°, then 68° for similar annealing/extension times. Unless otherwise stated, all of the experiments reported here used 24 cycles.

For reported results of comparison of conditions such as cycling temperatures and times, thermal cycler machines, thick and thin-walled tubes, etc., reactions were made up as 100 ul complete and then split into identical aliquots of 33 ul before subjecting to PCR cycling.

TABLE 3

Primer and template combinations.

| Product Size | Left Primer | Right Primer | Template DNA |
|---|---|---|---|
| 5.8 | MBL101 | MS1933 | λK138 |
| 6657 | MBL | MBR | λplac5 |
| 8386 | MBL-1.7 | MBR | λplac5 |
| 8.7 | MBR001 | λR36 | λK138 |
| 12.1 | lacZ333 | MBR202 | λK138 |
| 12.5 | MBL 27mer or MBL101 33mer | MBR 27mer or MBR202 33mer | λvacAI |
| 15560 | MSA19 28mer MSA1933 33mer | MBR202 | λplac5 |
| 18.0 | MBL101 | MBR202 | λK138 |
| 19.8 | L36 | MBL002 | λK138 |
| 20707 | MBL101 | λR36 36mer | λplac5 |
| 19584 | λL36 | lacZ333 | λplac5 |
| 13971 | MBR001 33mer | λR36 | λplac5 |
| 22.0 | λL36 | lacZ'533 | λK138 |
| 24.6 | λL36 | MSA1933 | λK138 |
| 22495 | λL36 | lacZ536 | λplac5 |
| 26194 | lacZ533 | λR36 | λplac5 |
| 28083 | L36 | MBL002 | λplac5 |
| 34968 | L36 | MBR202 | λplac5 |

Legend to Table 3

Product sizes in integer base pairs are as predicted from the sequence and structure of λ and λplac5 as documented in Genbank accession no. J02459 and ref. (21). Product sizes with decimal points in kb were determined by comparison with these products and with the λ+HindIII size standards labelled λH3. The sequence of the primers is given in the Sequence Listing.

Megaprimer consisted of gel-purified 384 bp PCR product DNA homologous to the region between the BamH1 site and EcoRI site of the gene coding for the CryV ICP of *Bacillus thuringiensis* (14), and primer-modified to remove these restriction sites. The PCR reactions in FIG. 4 each employed megaprimer (300 ng), primer BtV5 and 20 ng of genomic DNA from *Bacillus thuringiensis* strain NRD12 (15), and enzyme as indicated in the description above of FIG. 3. Cycling conditions were 30 sec. 95°, 7 min. 60°, for 20 cycles.

HindIII Digestion. Unfractionated, total PCR reactions for 28 and 35 kb targets were supplemented with 1/10 volume of 10XNaTMS (1×=50 mM NaCl, 10 mM Tris-HCl pH 7.7, 10 mM $MgCl_2$, 10 mM mercaptoethanol) and 2 ul (10 units) of restriction enzyme HindIII, and incubated at 55° C. for 90 min.

Test of exo− Pfu. Each 100 ul of reaction (incubated as 33 ul under 40 ul of oil) contained 2 ng λplac5 DNA as purified phage particles, 20 pmoles each of primers MBL-1.7 and MBR, reaction buffer PC2 and 1 ul of Klentaq-278 (0.7 ug), except for reaction 6, which contained 1 ul Pfu DNA polymerase (2.5 u.) alone. Other details are in the description of FIG. 12. Thermal conditions were 24 cycles of 2 sec. at 94°, 11 min. at 70°.

The discovery leading to the DNA polymerase mixture of the present invention was made during attempts to utilize in PCR a primer with a mismatched A-A base-pair at its 3' end. In fact the primer was itself a PCR product "megaprimer" of 384 bp, and the mismatched A had been added by Klentaq-278 using non-templated terminal transferase activity common to DNA polymerases (16). Neither Klentaq-278 (FIG. 3, lane 3) nor Pfu DNA polymerase (FIG. 3, lanes 1 & 2 and other levels of enzyme not shown) could catalyze amplification of the 1500 bp target that lay between the PCR-product megaprimer and a 42mer oligonucleotide primer. The combination of the two enzymes, however, was well able to catalyze amplification of the desired target fragment (FIG. 3, lane 4). Evidently, the Pfu DNA polymerase removed the presumed 3' A-A mismatch, allowing Klentaq-278 catalysis to proceed efficiently for each step of the PCR. The same result was obtained with Vent DNA polymerase substituted for Pfu (data not shown).

I hypothesized that mismatched 3'-ends are a general cause of inefficient primer extension during PCR of targets larger than a few kb. As a test system I employed a 6.6 kb lambda DNA target which was amplified detectably but poorly by AmpliTaq, Klentaq-278 or Pfu DNA polymerase in a variety of standard conditions. Per 100 ul reaction volume, 1 ul of Klentaq-278 was combined with various amounts of Pfu DNA polymerase, from ½ ul down to as little as 1/200 ul of Pfu. Since the Pfu stock (2.5 units/ul) was at least 10 times less concentrated than the Klentaq-278 stock (25-30 units/ul), the actual ratios tested were 1/20 to 1/2000 in DNA polymerase units. Representative results of these tests are shown in FIG. 1B. A high yield of target band was observed for all tested combinations of the two enzymes, yet several levels of each enzyme on its own failed to catalyze more than faintly detectable amplification. The lowest level of Pfu tested, 1/200 ul, exhibited only a slight beneficial effect. The apparent broad optimum ratio of Klentaq-278:Pful was 16 or 64 by volume, which is about 160 or 640 on the basis of DNA polymerase incorporation units. When tested at 6-8 kb (data not shown), other combinations of 3'-exo$^-$ and 3'-exo$^+$ thermostable DNA polymerases also showed the effect, including Klentaq-278/Vent, Klentaq5 (DeltaTaq, USB)/Pfu, Stoffel Fragment/Pfu, Klentaq-278/Deep Vent (our co-favorite; 48:1 by Volume, 720:1 by unit), and Pfu exo−/Pfu exo+. Amplitaq/Pfu or Amplitaq/Pwo, at ratio of 25:1, are also very effective, but it is important that the $Mg^{++}$ be held to a level that is close to 0.75 mM over the total level of dNTPs [for instance, 400 uM each dNTP, and 2.35 mM $MgCl_2$.]

A Very Short Heat Step is Preferred. I next attempted to amplify DNA in the size range 8.4 to 18 kb from lambda transducing phage template. Our early cycling protocol employed a denaturation step of 1 or 2 minutes at 950 or 98° C., but no useful product in excess of 8.4 kb was obtained until the parameters of this heat step were reduced to 2 sec. or 20 sec. at 93° or 94° C. In an experiment with the denaturation step at 94° for 20, 60, or 180 sec, the 8.4 kb product exhibited decreasing yield with increased length of this heat step (data not shown). Apparently, a component of the reaction is at its margin of thermostability. FIG. 2 shows that, using the short 2 sec. denaturation step, target fragment was obtained for some reactions at all sizes in the range 8.4 to 18 kb, with very high product yields up to 15 kb if 30 PCR cycles were employed. FIG. 2 also shows some failed reactions which I cannot explain. The failure mode that gives rise to massive ethidium staining in the sample well (30-cyclelane 2) was particularly common, especially at high enzyme levels.

Figure 4:
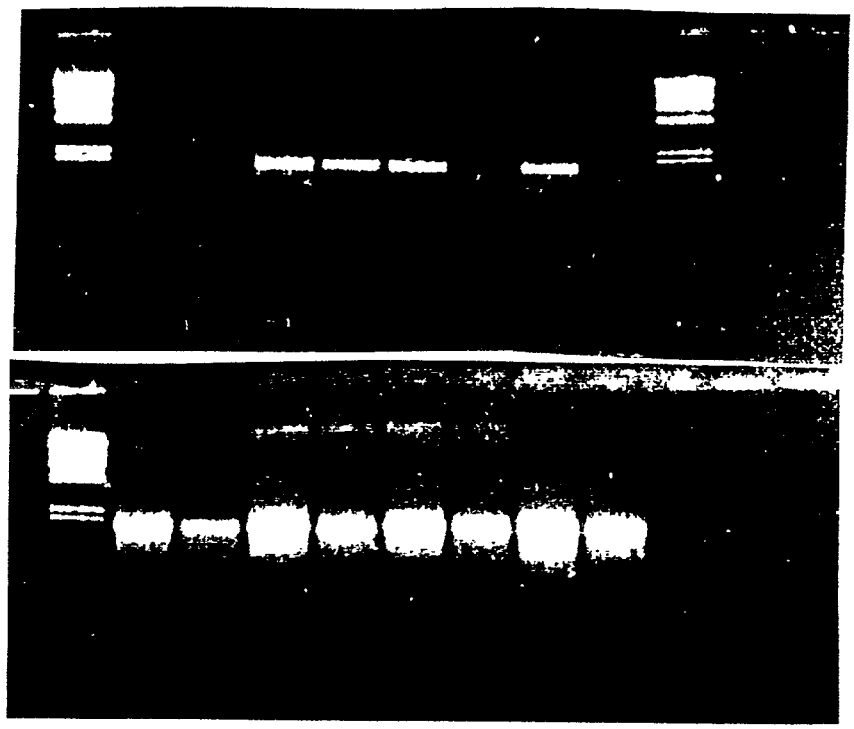
FIG. 4 is a depiction of an agarose gel demonstrating that 33mers are better than 27mers. Per 100 ul of reaction volume, 2 ng (lanes 1-6) or 10 ng (lanes 7-12) of lambda transducing phage template were amplified using 27mer primers (lanes 1-3, 7-9) or 33mer primers (lanes 4-6, 10-12). Besides being longer, the 33mer lambda primer sequences were situated 100 bp to the left of primer MBL and 200 bp to the right of primer MBR on the lambda genome. KlentaqLA-16 in the amounts of 1.2, 1.4, and 1.6 ul was used to catalyze the amplifications of 12.5, 15, and 18 kb, respectively. 15 ul aliquots (equivalent to 0.3 or 1.5 ng of λ template) were analyzed by 0.8% agarose electrophoresis.

Longer Primers. A change in primer length from 27 to 33 greatly reduced the frequency of failed reactions. FIG. 4 demonstrates improved reliability for amplification of 12.5, 15 and 18 kb with the longer 33 mer primers, under conditions of otherwise optimally high enzyme levels in which the 27mer primers failed to give rise to desirable target product. This result does not represent an extensive survey of primer length, and it has not yet been repeated with the improvements below. Therefore the optimum primer length for long PCR remains to be determined. Some of the amplifications analyzed in FIG. 5 utilized 36mer primers from the very ends of λ. A 2-5 min. preincubation at 68-72° (22) was necessary to release the template DNA from the phage particles and to fill in the sticky ends of lambda to complete the template homology with primers λL36 and λR36.

Filtered Tips. For repeated experiments in the same laboratory with the same primer sets, some sort of carry-over product can contaminate the pipetter barrels and stock solutions, and it is now believed that this is the main cause of the failed reactions shown in FIG. 4. The nature of the carried-over product has not yet been determined, but it seems to act as a "bad seed" to recruit good PCR product into the intractable material that is at the wells and does not enter the gel in the failed lanes of FIG. 4.

This carry-over contamination problem is effectively combated by two measures: 1) Always use different pipets for assembly (before cycling) and gel analysis (after cycling) procedures. 2) Always use the pipet tips with filters in each one, also known as aerosol resistant tips (ART).

When the above two measures are employed, 27 mer primers and primers as short as 23 base pairs often work well for the long and accurate PCr. When compared directly, 33 mer primers continue to outperform 23 mer primers, but the difference is now slight (less than 3-fold improvement).

Rapid Cycling. A change to thin-walled tubes, which have lower heat capacity and conduct heat more efficiently, further improved the reactions. FIG. 5 shows a CHEF pulse-field agarose gel analysis of successful amplifications of DNA spans 6-26 kb in size. The target of 28 kb was not amplifiable in the Omnigene thermal cycler (data not shown), but did appear (FIG. 6, lane 2) when the RoboCycler was employed.

Several models of thermal cycler have been employed, and although not all have been optimized, some are preferable to others for long PCR. As may be concluded from the advantage of thin-walled tubes noted above, success seems to be positively correlated with a high speed of temperature change made possible by the design of the thermal cycler. The RoboCycler achieves rapid temperature change by moving tubes from block to block, and observations with a thermistor temperature probe indicate that it raises the reactions to 93-95° for only 5 sec. under the denaturation conditions employed (30 sec. in the 99° block), before rapidly (within 30 sec) returning the reaction to 68°.

Higher pH. The current record 35 kb (FIG. 6, lane 3) was only amplifiable if the pH was increased. A preliminary scan of higher pH was carried out (data not shown), and this resulted in the appearance of the 35 kb band at pH 8.8 to 9.2, with the optimum at 9.1 as described in Methods (above).

Further improvement to a high yield of the 35 kb product was achieved by lengthening the extension time to 24 min. Other than the higher pH, the long PCR procedure has not yet realized any potential benefits from changes in buffer conditions from those optimized for 8.4 kb. For Targets over 20 kbs extension times exceeding 20 min. are preferred and the extension temperature is preferably below 69° C.

Identity of Long PCR Products. It can be seen in FIGS. 2, 4 and 5 that the mobilities of the successful large DNA products agree with those predicted in Table 3 from the known map positions of the primers used.

HindIII restriction enzyme digestion of the unpurified 28 and 35 kb products (FIG. 6, lanes 6 and 7) resulted in the expected left arm of lambda (23 kb) and 2.3 kb band from both, and the predictable bands terminated by the right PCR primer: 447 bp (barely visible) from the 28 kb product and 7331 bp from the 35 kb product.

Figure 7:
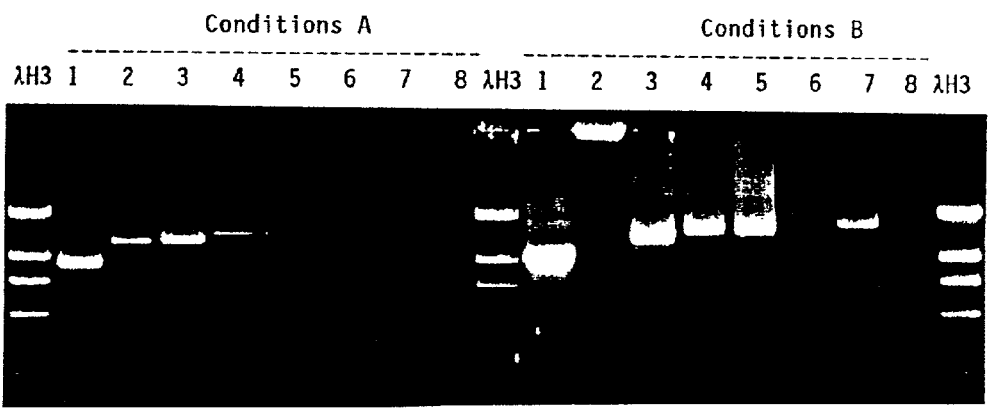
FIG. 7 is a depiction of an agarose gel showing the results of a Pfu exo⁻ mutant test. PCR amplification of 8.4 kb by 30 units (0.7 ug) of Klentaq-278 alone (lanes 1,7) and in combination with a very small admixture (1/16 ul or 1/64 ul, equivalent to 1/6 or 1/25 unit) of archaebacterial Pfu wild type exo⁺ DNA polymerase (+; lanes 2,3) or a mutant thereof lacking the 3'-exonuclease activity (−; lanes 4,5). Lane 6 is the result if 1 ul (2.5 units) of solely Pfu DNA polymerase (wt, exo⁺) being employed.
Figure 7:
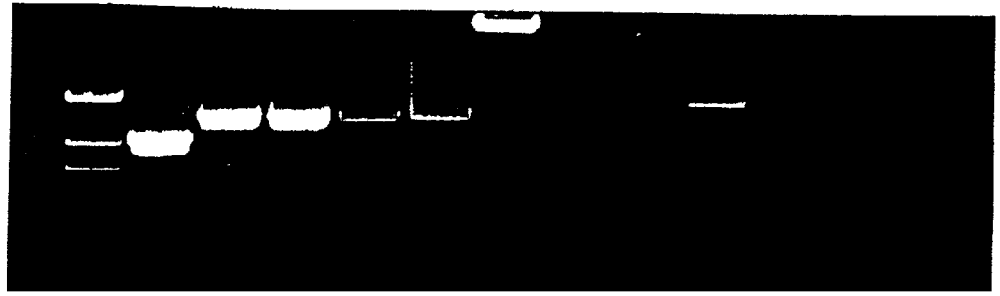

Exonuclease Mutant. The available mutant of Pfu DNA polymerase (8) which is defective in the 3'-exonuclease activity was tested. FIG. 7 shows that the 3'-exo⁻ mutant of Pfu DNA polymerase fails to promote efficient amplification of a long DNA target. This supports our hypothesis that the 3'-exonuclease activity is important for the efficiency of PCR amplification in this size range.

Fidelity test. Since the biological purpose of 3'-exonuclease is to edit base pair mismatches for high replication fidelity, we tested the fidelity of the PCR product using an assay involving the amplification and molecular cloning of an entire lacZ (β-galactosidase) gene flanked by two selectable markers (10). Heretofore the highest reported fidelity of PCR amplification is that catalyzed by Pfu DNA polymerase (2). Table 4 shows that the fidelity of the product amplified by the 640:1 mixture of Klentaq-278 and Pfu DNA polymerase at least matches that obtained for Pfu DNA polymerase, alone, when each are used for 16 cycles of PCR. Our designation of the enzyme mixture as Klentaq-LA (KlenTaq Long and Accurate) reflects this high fidelity performance.

TABLE 4

Non-silent mutations introduced into the lacZ gene by 16 cycles of PCR (10).

| Enzyme | LacZ + Blue or White | LacZ − Light Blue | % mutant | Effective cycle no. (c) | Errors per $10^5$ bp (b) | Fold Improvement over full-length Taq |
|---|---|---|---|---|---|---|
| KTLA-64 | 571 | 34 | 5.6 | 12 | 1.05 | 12.7 |
| Pfu | 528 | 37 | 6.5 | 8 | 1.9 | 6.9 |
| Klentaq5 (a) | 442 | 85 | 16.1 | 8 | 5.1 | 2.6 |
| Klentaq1 | 3225 | 985 | 26.4 | 8 | 9.0 | 1.5 |
| Amplitaq | 525 | 301 | 36.4 | 8 | 13.4 | 1.0 |

(a) Klentaq[5] is the N-terminal deletion of Taq DNA polymerase described in ref. 10.
(b) Equation 1 of reference 10 was rearranged to be as follows to solve for errors per bp: $X = -(\ln(2F^{(1/m-1)} - 1))/1000$, where X is the errors per bp incorporated, 1000 is the effective target size in the lacZ gene (10), F is the fraction of blue colonies, and m is the effective cycle number.
(c) As in ref. 10, the effective cycle number was estimated at less than the machine cycles to reflect the actual efficiency of the reaction, yet higher than the minimum calculated from the fold-amplification. Strand loss due to incomplete synthesis of product strands is a probable cause of lower than ideal amplification efficiency. Therefore successful (not lost) product molecules are judged to have undergone more than the calculated minimum number of replications. KTLA-64 (Klentaq-278:Pfu::64:1 by volume) was assigned a higher effective cycle number since its reactions started with 10 times less DNA (1.5 ng vs. 15 ng plasmid pWB305) to result in comparable levels of product.

Discussion

The previous length limitation for PCR amplification is postulated to have been caused by low efficiency of extension at the sites of incorporation of mismatched base pairs. Although it would have seemed that the cure for these mismatches would be to employ enzymes with 3'-(editing)-exonucleases, I believe that when Pfu and Vent DNA polymerase are used to catalyze our amplifications on their own, their failure is due to degradation of the PCR primers by their 3'-exonucleases, especially during the required long synthesis times and at optimally high DNA polymerase levels. Evidently, low levels of 3'-exonuclease are sufficient and optimal for removal of the mismatches to allow the Klentaq-278 and amplification to proceed. It has been demonstrated that the optimally low level of 3'-exonuclease can be set effectively, conveniently, and flexibly by mixing and dilution.

Preferably the ratio of exo–/exo+ enzyme is high. If equal levels of the two types of enzymes are used (or where the E2 component is in excess), and in many embodiments tested, where the ratio of exo–/exo+ is 4 or less, the effectiveness of the long PCR, even under optimal cycling conditions discussed below, is non-existent or much reduced.

It is preferred, and for certain applications, important that the length and temperature of the heat denaturation step of the PCR be kept to a minimum. Further, the improvement obtained by increasing the pH slightly may correspond to a decrease in template depurination. If so, further improvements may result if depurination can be reduced, or if a majority DNA polymerase component can be found which is able to bypass depurination sites.

The short denaturation time found to be optimal, preferably less than 20 sec., and most preferably, 5 sec. or less in the reaction itself at 95°, is surprisingly effective for the amplification of 35 kb, whereas it might have been expected that longer PCR targets would need longer denaturation time to become completely denatured. If complete denaturation is required for PCR, and if longer DNA requires more time to unwind at 95°, the required unwinding time may eventually become significantly more than 5 seconds. This could limit the size of amplifiable product because of the increased depurination caused by longer denaturation times.

These amplifications were successful with several different target sequences, with several primer combinations, and with product sizes up to nearly twice the maximum size of inserts cloned into λ. Whole viruses and plasmids up to 35 kb in length should now be amplifiable with this system. Should this method prove applicable to DNA of higher complexity than λ, it could prove a boon to genomic mapping and sequencing applications, since in vitro amplification is convenient and avoids the DNA rearrangement and gene toxicity pitfalls of in vivo cloning.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

REFERENCES

1. Saiki, R. K., Gelfand, D. H., Stoffel, S., Scharf, S. J., Higuchi, R., Horn, G. T., Mullis, K. B., and Erlich, H. A. (1988) *Science* 239, 487-491.
2. Lundberg, K. S., Shoemaker, D. D., Adams, M. W. W., Short, J. M. Sorge, J. A., and Mathur, E. J. (1991) *Gene* 108, 1-6.
3. Lawyer, F. C., Stoffel, S., Saiki, R. K., Chang, S -Y., Landre, P. A., Abramson, R. D., and Gelfand, D. H. (1993) *PCR Methods and Applications* 2, 275-287.
4. Jeffreys, A. J., Wilson, V., Neumann, R., and Keyte, J. (1988) *Nucleic Acids Res.* 16, 10953-10971.
5. Krishnan, B. R., Kersulyte, D., Brikun, I., Berg, C. M. & Berg, D. E. (1991) *Nucleic Acids Res.* 19, 6177-6182.
6. Maga, E. A., & Richardson, T. (1991) *BioTechniques* 11: 185-186.
7. Ohler, L. D. & Rose, E. A. (1992) *PCR Methods and Applications* 2, 51-59.
8. Rychlik, W., Spencer, W. J., and Rhoads, R. E. (1990) *Nucleic Acids Res.* 18: 6409.
9. Kainz, P. Schmiedlechner, A., & Strack, H. B. (1992) *Analytical Biochem.* 202, 46-49.
10. Barnes, W. M. (1992) *Gene* 112, 29-35.
11. Chu, G. D., Vollrath, D. and Davis, R. W. (1986) *Science* 234, 1582-.
12. Ippen, K., Shapiro, J. A., and Beckwith, J. R. (1971) *J.Bact.* 108, 5-9.
13. Kohara, Y. (1990) pp 29-42 in *The Bacterial Chromosome*, eds Drlica, K. & Riley, M., ASM Washington D.C.
14. Tailor, R., Tippett, J., Gibb, G., Pells, S., Pike, D., Jordan, L., Ely, S. (1992) *Mol. Microbiol.* 6, 1211-1217.
15. Dubois, N. R. Reardon, R. C., Kolodny-Hirsh, D. M. *J.Econ.Entomol.* 81, 1672 (1988)],18.
16. Clark, J. M. (1988) *Nucleic Acids Res.* 16, 9677-.
17. Brewer, A. C., Marsh, P. J and Patient, R. K. (1990) *Nucleic Acids Res.* 18, 5574.
18. Lindahl, T. (1993) *Nature* 362: 709-715.
19. Lindahl, T. & Nyberg, B. (1972) *Biochemistry* 11: 3611-3618.
20. Sigma Chemical Co. Technical Bulletin No. 106B.
21. Shpakovski, G. V., Akhrem, A. A., and Berlin, Y. A. (1988) *Nucleic Acids Res* 16, 10199 (1988).

---

What is claimed is:

1. A kit for the synthesis of a polynucleotide, said kit comprising A mixture comprising:
   (a) a first DNA polymerase, wherein said first polymerase possesses 3'-5' exonuclease activity selected from the group consisting of Archaebacterial DNA polymerases, and
   (b) a second DNA polymerase, wherein said second polymerase lacks 3'-5' exonuclease activity selected from the group consisting of thermostable DNA polymerases lacking 3'-5' exonuclease activity; wherein the ratio of DNA polymerase activity of the first DNA polymerase to the DNA polymerase activity of the second DNA polymerase is from about 1:100 up to about 1:600.

2. A kit according to claim 1, wherein said *Thermus aquaticus* DNA polymerase is selected from the group consisting of wild-type *Thermus aquaticus* DNA polymerase and N-terminal deleted forms of the same enzyme.

3. A kit according to claim 1, wherein said first DNA polymerase comprises *Pyrococcus furiosus* DNA polymerase.

4. A kit according to claim 1, wherein said second DNA polymerase comprises *Thermus aquaticus* DNA polymerase.

5. A kit according to claim 2, wherein said *Thermus aquaticus* DNA polymerase comprises Klentaq-278 DNA polymerase.

* * * * *

UNITED STATES PATENT AND TRADEMARK OFFICE
CERTIFICATE OF CORRECTION

| | | |
|---|---|---|
| PATENT NO. | : 7,452,665 B2 | Page 1 of 1 |
| APPLICATION NO. | : 09/981002 | |
| DATED | : November 18, 2008 | |
| INVENTOR(S) | : Wayne M. Barnes | |

It is certified that error appears in the above-identified patent and that said Letters Patent is hereby corrected as shown below:

Column 45, lines 1-4, cancel the text beginning with "2. A kit according to claim 1" to and ending with "same enzyme." and insert the following claim:
--2. A kit according to claim 1, wherein said second DNA polymerase comprises Thermus aquaticus DNA polymerase.--

Column 45, lines 5-7, cancel the text beginning with "3. A kit according to claim 1" to and ending with "DNA polymerase." and insert the following claim:
--3. A kit according to claim 2, wherein said Thermus aquaticus DNA polymerase is selected from the group consisting of wild-type Thermus aquaticus DNA polymerase and N-terminal deleted forms of the same enzyme.--

Column 46, lines 1-2, cancel the text beginning with "4. A kit according to claim 1" to and ending with "DNA polymerase." and insert the following claim:
--4. A kit according to claim 1, wherein said first DNA polymerase comprises Pyrococcus furiosus DNA polymerase.--

Signed and Sealed this

Tenth Day of February, 2009

JOHN DOLL
*Acting Director of the United States Patent and Trademark Office*